United States Patent [19]

Gandolfi et al.

[11] 4,195,183
[45] Mar. 25, 1980

[54] OMEGA-NOR-AROMATIC-13,14-DEHYDRO-PROSTAGLANDINS AND PROCESS FOR THEIR PREPARATION

[75] Inventors: Carmelo Gandolfi; Franco Faustini; Walter Moretti; Mario M. Userdi; Roberto Cesercini, all of Milan, Italy

[73] Assignee: Farmitalia Certo Erba S.p.A., Milan, Italy

[73] Assignee: Farmitalia Certo Erba S.p.A., Milan,

[22] Filed: May 2, 1978

Related U.S. Application Data

[62] Division of Ser. No. 833,609, Sep. 15, 1977, which is a division of Ser. No. 786,802, Apr. 12, 1977.

[30] Foreign Application Priority Data

Jun. 1, 1976 [IT] Italy .................................. 23826 A/76
Dec. 16, 1976 [IT] Italy .................................. 30458 A/76

[51] Int. Cl.$^2$ .......................................... C07C 177/00
[52] U.S. Cl. ...................................... 560/53; 424/808; 560/9; 562/426; 562/465
[58] Field of Search .................... 560/9, 53; 562/426, 562/465

[56] References Cited

PUBLICATIONS

Derwent Abstract, 86544y/49, BE 855.236, 1/6/76.
Derwent Abstract, 03258y/02, NL 7606.825, 6/23/75.

*Primary Examiner*—Paul J. Killos
*Attorney, Agent, or Firm*—Cushman, Darby & Cushman

[57] ABSTRACT

$PGF_\alpha$ compounds are disclosed having as the lower side chain

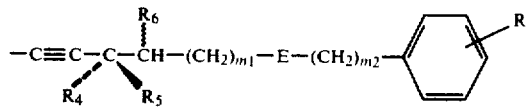

in which one of $R_4$ and $R_5$ hydroxyl and the other is alkoxy $R_6$ is hydrogen or alkyl, m is 0-3, E represents oxygen or sulphur and R is hydrogen, halogen, alkyl, alkoxy or trihaloalkyl.

3 Claims, No Drawings

ω-NOR-AROMATIC-13,14-DEHYDRO-PROSTA-GLANDINS AND PROCESS FOR THEIR PREPARATION

CROSS-REFERENCE TO RELATED APPLICATIONS

This application is a divisional of our application Ser. No. 833,609 filed Sept. 15, 1977, which in turn is a divisional of application Ser. No. 786,802, filed Apr. 12, 1977.

The present invention relates to ω-nor-aromatic-13,14-dehydro-prostaglandins to a method for their preparation and to pharmaceutical and veterinary compositions containing them.

The compounds of the invention are optically active or racemic prostaglandins of formula (I)

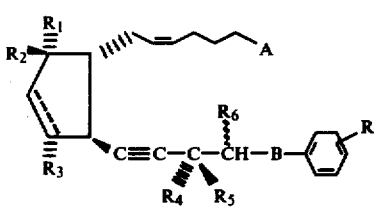

wherein

A is a member selected from the group consisting of (a) —$CH_2OH$; (b) —$COOR_a$, wherein $R_a$ is hydrogen, a $C_1$–$C_{12}$ alkyl group or a cation of a pharmaceutically or veterinarily acceptable base; (c)

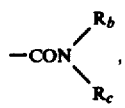

wherein $R_b$ and $R_c$ are independently selected from the group consisting of hydrogen, $C_1$–$C_6$ alkyl and phenyl; the symbol $\rightleftharpoons$ represents a single or a double bond, wherein, when the symbol $\rightleftharpoons$ is a double bond, $R_3$ is a hydrogen atom and $R_1$ and $R_2$ together form an oxo group, while, when the symbol $\rightleftharpoons$ is a single bond, $R_3$ is hydroxy and one of $R_1$ and $R_2$ is hydrogen and the other is hydroxy or acyloxy or $R_1$ and $R_2$, taken together, form an oxo group;

one of $R_4$ and $R_5$ is hydrogen and the other is hydroxy, $C_1$–$C_6$ alkoxy or aralkoxy;

$R_6$ is hydrogen or $C_1$–$C_4$ alkyl;

B is —$(CH_2)_n$— or —$(CH_2)_{m1}$—E—$(CH_2)_{m2}$—, wherein each of n, $m_1$ and $m_2$ is independently zero, 1, 2 or 3 and E is oxygen or sulphur;

R is a member selected from the group consisting of (a') $C_1$–$C_6$ alkyl; (b') $C_1$–$C_6$ alkoxy; (c') $C_1$–$C_6$ trihaloalkyl; (d') halogen; (e') amino; (f')

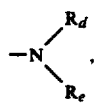

wherein $R_d$ and $R_3$ are independently selected from the group consisting of hydrogen, phenyl, benzoyl, $C_1$–$C_6$ alkyl, $C_1$–$C_6$ aliphatic acyl; (g') phenyl, unsubstituted or substituted by one or more substituents selected from the group consisting of $C_1$–$C_6$ alkoxy and halogen; and (h') phenoxy, unsubstituted or substituted by one or more substituents selected from the group consisting of $C_1$–$C_6$ alkoxy and halogen.

The double bond in the 5(6)-position is a cis-double bond.

In the formulae of this specification, the broken lines ( ||||| ) indicate that the substituents are in the α-configuration, i.e. are below the plane of the ring or of the chain, while the heavy solid lines (———) indicate that the substituents are in the β-configuration, i.e. above the plane of the ring or of the chain; the wavy line attachment ( $\xi$ ) indicates that the groups may be either in the α-configuration, or in the β-configuration.

As is evident from formula (I), the hydroxy group, or respectively the $C_1$–$C_6$ alkoxy or the aralkoxy group, linked to the carbon atom in the 15-position may be either in the α-configuration

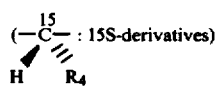

or in the β-configuration

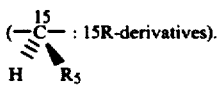

When on the carbon atom in the 16-position there is a $C_1$–$C_4$ alkyl group, said substituent may be either a 16S-alkyl (α-configuration) or a 16R-alkyl (β-configuration) or a 16(S,R)-alkyl, i.e. the mixture of the two 16S- and 16R-diastereoisomers.

It is also evident that when the symbol $\rightleftharpoons$ represents a double bond and therefore $R_3$ is a hydrogen atom, this hydrogen atom, being linked to a carbon atom which is no more asymmetric, may be obviously in an only one fixed position, i.e. on the plane of the ring, and therefore it may be neither in the α-position (i.e. below the plane of the ring) nor in the β-position (i.e. above the plane of the ring).

The alkyl and alkoxy groups may be branched or straight chain groups. When $R_a$ is a $C_1$–$C_{12}$ alkyl, it is preferably methyl, ethyl or heptyl; n is preferably 1, $m_1$ is preferably 1 and $m_2$ is preferably zero. When one of $R_1$ and $R_2$ is acyloxy, it is preferably a $C_2$–$C_6$ alkanoyloxy group, e.g. acetoxy and propionyloxy, or a benzoyloxy group. When R is a $C_1$–$C_6$ trihaloalkyl group, it is preferably trifluoromethyl.

When R is

wherein $R_d$ and/or $R_e$ is a $C_1$–$C_6$ aliphatic acyl, the aliphatic acyl group is preferably $C_2$–$C_6$ alkanoyl.

When one of $R_4$ and $R_5$ is $C_1$–$C_6$ alkoxy, it is preferably $C_1$–$C_3$ alkoxy, in particular methoxy.

When one of $R_4$ and $R_5$ is aralkoxy, in the aralkoxy group the alkoxy is preferably a $C_1$–$C_6$ alkoxy and the aryl is preferably phenyl. In particular, when one of $R_4$ and $R_5$ is aralkoxy, it is preferably benzyloxy. $R_6$ is preferably hydrogen.

When $R_6$ is $C_1$–$C_4$ alkyl, the alkyl group is preferably methyl.

Examples of cations of pharmaceutically or veterinarily acceptable bases are either metallic cations or organic amine cations.

Particularly preferred metallic cations are those deriving from alkaline bases, e.g. lithium, sodium and potassium, and from earth-alkaline bases, e.g. magnesium and calcium, although also metallic cations deriving from other bases, e.g. aluminium, zinc and iron, are comprised in the scope of the invention.

Examples of cations deriving from organic amines are those deriving from methylamine, dimethylamine, trimethylamine, ethylamine, dibutylamine, N-methylhexylamine, decylamine, dodecylamine, allylamine, cyclopentylamine, cyclohexylamine, benzylamine, dibenzylamine, α-phenyl-ethylamine, β-phenyl-ethylamine, ethylenediamine, diethylenetriamine, morpholine, piperidine, pyrrolidine, piperazine, as well as the alkyl derivatives of the latter four bases, mono-, di- and tri-ethanolamine, ethyl-diethanolamine, N-butyl-ethanolamine, 2-amino-1-butanol, 2-amino-2-methyl-1-propanol, N-phenyl-ethanolamine, galactamine, N-methyl-glucamine, N-methyl-glucosamine, ephedrine, procaine, lysine and dehydroabietilamine.

The nor-compounds are those wherein n, or respectively $m_1$, are 3; the dinor-compounds are those wherein n, or respectively $m_1$, are 2; the trinor-compounds are those wherein n, or respectively $m_1$, are 1; the tetranor-compounds are those wherein n, or respectively $m_1$, are zero.

Examples of preferred compounds of the invention are the following:

5c-9α,11α,15S-trihydroxy-20,19,18-trinor-17-phenyl-prost-5-en-13-ynoic acid;

5c-9α,11α-dihydroxy-15S-methoxy-20,19,18-trinor-17-phenyl-prost-5-en-13-ynoic acid;

5c-9α,11α,15S-trihydroxy-20,19,18-trinor-17-(4'-fluoro)-phenyl-prost-5-en-13-ynoic acid;

5c-9α,11α,15S-trihydroxy-20,19,18-trinor-17-(3'-chloro)-phenyl-prost-5-en-13-ynoic acid;

5c-9α,11α,15S-trihydroxy-20,19,18-trinor-17-(3'-trifluoromethyl)-phenyl-prost-5-en-13-ynoic acid;

5c-9β,11α,15S-trihydroxy-20,19,18-trinor-17-phenyl-prost-5-en-13-ynoic acid;

5c-9α,11α,15S-trihydroxy-20,19,18-trinor-17-phenyl-prost-5-en-13-ynoic acid-9α-benzoate;

5c-9α,11α,15S-trihydroxy-20,19,18-trinor-17-cyclohexyl-prost-5-en-13-ynoic acid-9α-propionate;

5c-9α,11α,15S-trihydroxy-20,19-dinor-18-phenyl-prost-5-en-13-ynoic acid;

5c-9α,11α,15S-trihydroxy-20,19,18,17-tetranor-16-phenyl-prost-5-en-13-ynoic acid;

5c-9α,11α,15S-trihydroxy-20,19,18,17-tetranor-16-phenoxy-prost-5-en-13-ynoic acid;

5c-9α,11α,15S-trihydroxy-20,19,18,17-tetranor-16-(4'-fluoro)-phenoxy-prost-5-en-13-ynoic acid;

5c-9α,11α,15S-trihydroxy-20,19,18,17-tetranor-16-(3'-chloro)-phenoxy-prost-5-en-13-ynoic acid;

5c-9α,11α,15S-trihydroxy-20,19,18,17-tetranor-16-(3'-trifluoromethyl)-phenoxy-prost-5-en-13-ynoic acid;

5c-9α,11α,15S-trihydroxy-20,19,18,17-tetranor-16-(2'-fluoro)-phenoxy-prost-5-en-13-ynoic acid;

5c-9α,11α,15S-trihydroxy-20,19,18,17-tetranor-16-(2'-methoxy)-phenoxy-prost-5-en-13-ynoic acid;

5c-9α,11α,15S-trihydroxy-20,19,18,17-tetranor-16S-methyl-16-phenoxy-prost-5-en-13-ynoic acid;

5c-9α,11α,15S-trihydroxy-20,19,18,17-tetranor-16R-methyl-16-phenoxy-prost-5-en-13-ynoic acid;

5c-9-oxo-11α,15S-dihydroxy-20,19,18-trinor-17-phenyl-prost-5-en-13-ynoic acid;

5c-9-oxo-11α,15S-dihydroxy-20,19,18,17-tetranor-16S-methyl-16-phenoxy-prost-5-en-13-ynoic acid;

5c-9-oxo-11α,15S-dihydroxy-20,19,18,17-tetranor-16R-methyl-16-phenoxy-prost-5-en-13-ynoic acid, as well as the salts and the lower alkyl esters thereof.

The compounds of the invention are prepared by a process comprising reacting an optically active compound, or a racemic mixture of compounds, of formula (II)

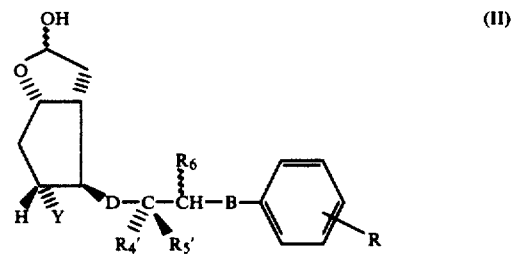

wherein B, $R_6$ and R are as defined above, D is —C≡C— or —CH=CX—, wherein X is bromine, chlorine or iodine, Y is hydroxy or a known protecting group bound to the ring by an ethereal oxygen atom, and one of $R'_4$ and $R'_5$ is hydrogen and the other is hydroxy, $C_1$–$C_6$ alkoxy, aralkoxy, or a known protecting group bound to the chain by an ethereal oxygen atom, with a Wittig reagent comprising a group of formula —(CH$_2$)$_4$—A', wherein A' is a member selected from the group consisting of (a") —CH$_2$Z, wherein Z is hydroxy or a known protecting group bound to the chain by an ethereal oxygen atom; (b") —COOR'$_a$, wherein R'$_a$ is a hydrogen atom or a $C_1$–$C_{12}$ alkyl group;

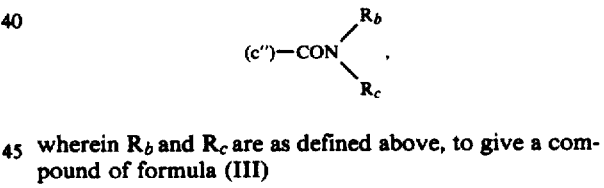

wherein $R_b$ and $R_c$ are as defined above, to give a compound of formula (III)

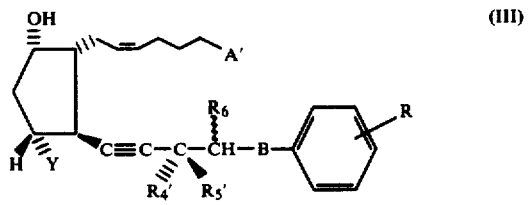

wherein, A', Y, $R'_4$, $R'_5$, $R_6$, B and R are as defined above, which, when Z, if present, and Y are known protecting groups as defined above, and one of $R'_4$ and $R'_5$ is $C_1$–$C_6$ alkoxy, aralkoxy or a known protecting group as defined above and the other is hydrogen, may be optionally esterified to give the 9α- or 9β-acyloxy derivative, and then, after optional selective saponification of the 9β-acyloxy derivative to give the 9β-hydroxy derivative, removing the known protecting groups in a compound of formula (III), wherein Z, if present, and Y are known protecting groups as defined above and/or one of $R'_4$ and $R'_5$ is a known protecting group as defined above and the other is hydrogen, or removing the known protecting groups as defined above in the 9α- or 9β-acyloxy derivative of the compound of formula (III), so obtaining a compound of formula (I), wherein R₃ is hydroxy, the symbol ═══ is a single bond, one of R₁ and R₂ is hydrogen and the other is hydroxy or acyloxy, and one of R₄ and R₅ is hydroxy, C₁-C₆ alkoxy or aralkoxy and the other is hydrogen, or, if desired, oxidizing the 9α- or 9β-hydroxy group in a compound of formula (IV)

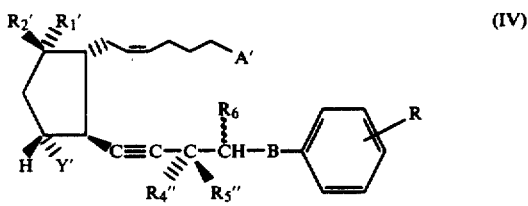

wherein A', R₆, B and R are as defined above, one of R'₁ and R'₂ is hydrogen and the other is hydroxy, Z, if present, and Y' are known protecting groups as defined above, one of R"₄ and R"₅ is hydrogen and the other is C₁-C₆ alkoxy, aralkoxy or a known protecting group as defined above, to give a compound of formula (V)

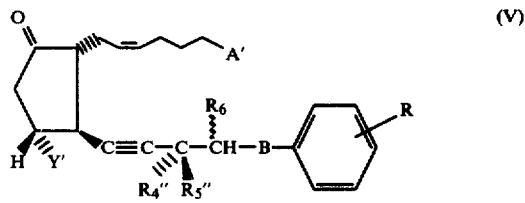

wherein A', Y', R"₄, R"₅, R₆, B and R are as defined above, which, in turn, is subjected to the removal of the protecting groups, to give, according to the reaction conditions used, either a compound of formula (I), wherein the symbol ═══ is a single bond, R₃ is hydroxy and R₁ and R₂, taken together, form an oxo group, or a compound of formula (I), wherein the symbol ═══ is a double bond, R₃ is hydrogen, and R₁ and R₂ together form an oxo group, and/or, if desired, converting a compound of formula (I), wherein one of R₄ and R₅ is hydrogen and the other is hydroxy, and wherein the hydroxy groups in the 1- and/or 9- and/or 11-positions, when present, are protected as described above, into a compound of formula (I) wherein one of R₄ and R₅ is hydrogen and the other is C₁-C₆ alkoxy or aralkoxy, and then removing, if present, the protecting groups, and/or, if desired, reacting a compound of formula (I), wherein A is —COOR$_a$, wherein R$_a$ is hydrogen, and the hydroxy groups in the 1-, 9-, 11- and/or 15-positions are optionally protected as described above, with a base, followed, if required, by removal of the protecting groups, to give a compound of formula (I) wherein A is —COOR$_a$, wherein R$_a$ is a cation of a pharmaceutically or veterinarily acceptable base, or esterifying a compound of formula (I), wherein A is —COOR$_a$, wherein R$_a$ is hydrogen and the hydroxy groups in the 1-, 9-, 11- and/or 15-positions are optionally protected as described above, followed, if required, by removal of the protecting groups, to give a compound of formula (I), wherein A is —COOR$_a$, wherein R$_a$ is C₁-C₁₂ alkyl, or hydrolysing a compound of formula (I), wherein A is —COOR$_a$, wherein R$_a$ is C₁-C₁₂ alkyl and the hydroxy groups in the 1-, 9-, 11- and/or 15-positions are optionally protected as described above, followed, if required, by removal of the protecting groups, to give a compound of formula (I), wherein A is —COOR$_a$, wherein R$_a$ is hydrogen, or reacting a compound of formula (I), wherein A is —COOR$_a$, wherein R$_a$ is hydrogen or C₁-C₁₂ alkyl and the hydroxy groups in the 1-, 9-, 11- and/or 15-positions are optionally protected as described above, with a compound of formula

wherein R$_b$ and R$_c$ are as defined above, followed, if required, by removal of the protecting groups, to give a compound of formula (I), wherein A is

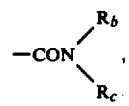

wherein R$_b$ and R$_c$ are as defined above.

The known protecting groups (i.e. ether groups) should be convertible to hydroxy groups under mild reaction conditions, e.g. acid hydrolysis. Examples are acetalic ethers, enolethers and sylylethers. The preferred groups are

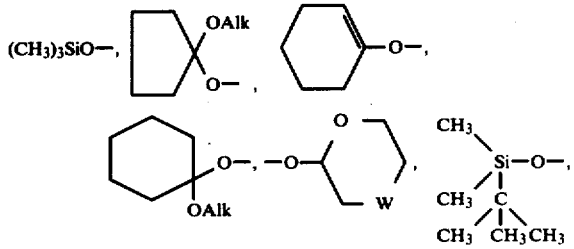

wherein W is —O— or —CH₂—, and Alk is a lower alkyl group. When in the lactol of formula (II) D is —C≡C— or —CH═CX—, wherein X is bromine or iodine, the Wittig reaction may be performed using about two moles of Wittig reagent per mole of lactol and it is sufficient that the reaction lasts 10–20 minutes. When in the lactol of formula (II) D is —CH═CX—, wherein X is chlorine, it is necessary, by using for example 1.5 to 2.5 moles of Wittig reagent per mole of lactol, to prolong the reaction time up to ten hours or, if it is desired to use shorter reaction times, it is necessary to employ a great excess of Wittig reagent (at least 5 moles of Wittig reagent per mole of lactol for reaction times of about 30 minutes). Therefore, when in the lactol of formula (II) D is —CH═CX—, X is preferably bromine or iodine.

When in the lactol of formula (II) D is —CH═CX—, wherein X is bromine, chlorine or iodine, the hydrogen atom linked to the carbon atom in the 13- position and the halogen atom linked to the carbon atom in the 14- position may be either in the trans-position (geometric trans-isomers) or in the cis-position (geometric cis-isomers). Preferably they are in the trans-position.

The Wittig reaction is performed by using the conditions generally followed for this kind of reaction, i.e. in an organic solvent, for example diethylether, hexane, dimethylsulphoxide, tetrahydrofuran, dimethylformamide or hexamethylphosphoramide, in presence of a base, preferably sodium hydride and potassium tert.butoxide, at 0° C. to the reflux temperature of the reaction mixture, preferably at room temperature or below.

The term "Wittig reagent" includes compounds of general formula

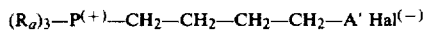

wherein $R_a$ is aryl or alkyl, Hal is halogen, e.g. bromine or chlorine and A' is as defined above. When $R_a$ is aryl, it is preferably phenyl. When $R_a$ is alkyl, it is preferably ethyl.

The preparation of the Wittig reagent is discussed in detail by Tripett, Quart. Rev., 1963, XVII, No. 4, 406.

When in the lactol of formula (II) D is —CH=CX—, wherein X is bromine, chlorine or iodine, during the reaction with the Wittig reagent, the dehydrohalogenation takes place as easily when the hydrogen atom linked to the carbon atom in the 13- position and the halogen atom linked to the carbon atom in the 14- position are in the trans-position as when they are in the cis-position.

The optional acylation of the 9α- hydroxy group in the compound of formula (III) may be performed in a conventional manner, for example by treatment with an anhydride or a halide, e.g. a chloride of a carboxylic acid in presence of a base. In this case, a 9α- acyloxy derivative is obtained.

On the contrary, when the acylation of the 9α- hydroxy group in the compound of formula (III) is carried out with a carboxylic acid in presence of a compound of formula $M^vY_3$, wherein $M^v$ is a metalloid of the V group and Y is an alkyl, a dialkylamino or an aryl group, and of a hydrogen-acceptor agent, a 9β- acyloxy derivative is obtained, that is, in the latter case, the esterification involves the complete inversion of configuration of the hydroxy group in the 9- position. This reaction is preferably carried out at room temperature in an inert anhydrous solvent, preferably selected from the group consisting of aromatic hydrocarbons, such as benzene and toluene, linear or cyclic ethers, for example diethyl ether, dimethoxyethane, tetrahydrofuran and dioxan.

All the used reagents, that are the compounds of formula $M^vY_3$, the esterifying carboxylic acid and the hydrogen-acceptor agent, are preferably employed in the proportion of at least 1.5 mole per each mole of alcohol; 2 to 4 moles of the reagents per each mole of alcohol are preferably used.

In the compound of formula $M^vY_3$, $M^v$ is preferably P, As, Sb, especially P. Again in the same compound, when Y is alkyl, it is preferably methyl, while when Y is aryl, it is preferably phenyl; when Y is dialkylamino, it is preferably dimethylamino. The compound of formula $M^vY_3$ is preferably selected from the group consisting of triphenylphosphine, triphenylarsine, triphenylstibine and hexamethyltriaminophosphine of formula $[(CH_3)_2N]_3P$.

The hydrogen-acceptor used is preferably an ester or an amide of the azodicarboxylic acid, preferably ethyl azodicarboxylate, but also other hydrogen-acceptors may be used, for instance 2,3,5,6-tetrachloro-benzoquinone, 2,3-dicyano-5,6-dichloro-benzoquinone or azobisformamide.

The optional saponification of the 9β-acyloxy derivative to give the corresponding 9β-hydroxy derivative may be effected in a conventional way, e.g. by treatment with sodium or potassium hydroxide in an aqueous or alcoholic/aqueous solution, so obtaining also the saponification of the eventually present ester group in the 1-position. If it is desired to saponify one of the 9β-acyloxy group to give the corresponding 9β-hydroxy derivative, it is preferable to carry out the saponification by treatment with a dry base, e.g. potassium or sodium carbonate, in a dry alcohol, e.g. a lower aliphatic alcohol, such as methanol.

The removal of the known protecting groups bound to the ring, or respectively to the chain, by an ethereal oxygen atom is, whenever required, performed under conditions of mild acid hydrolysis, for example with a mono- or poly-carboxylic acid, e.g. formic, acetic, oxalic, citric and tartaric acid, and in a solvent, for example, water, acetone, tetrahydrofuran, dimethoxyethane and lower aliphatic alcohols or with a sulfonic acid, e.g. p-toluene-sulfonic acid in a solvent such as a lower aliphatic alcohol, e.g. in dry methanol or in dry ethanol or with a polystyrenesulfonic resin. For example, 0.1 to 0.25 N poly-carboxylic acid (e.g. oxalic or citric acid) is used in the presence of a convenient low boiling co-solvent which is miscible with water and which can be easily removed in vacuo at the end of the reaction. The oxidation of the 9α- or 9β-hydroxy group to yield an oxo group may be carried out with, for example, Jones reagent or Moffatt reagent.

As stated above, the removal of the known protecting groups in a compound of formula (IV) may give, according to the reaction conditions used, either a compound of formula (I), wherein the symbol ≡≡≡ is a single bond, $R_3$ is hydroxy and $R_1$ and $R_2$, taken together, form an oxo group, or a compound of formula (I), wherein the symbol ≡≡≡ is a double bond, $R_3$ is hydrogen and $R_1$ and $R_2$, taken together, form an oxo group.

The former compound is obtained as the only product, by operating at temperatures ranging between about 25° C. and about 35°-38° C., while by operating at higher temperatures, for example, at the reflux temperature for about 3 hours, the latter compound is obtained as the only product. The subsequent optional reactions, i.e. etherification of the 15-hydroxy group, the salification, the esterification, the saponification and the conversion of an acid or an ester to an amide, may be carried out by conventional methods.

Thus, the etherification of the 15-hydroxy group may be carried out for example by reaction with an optionally aryl-substituted diazoalkane in presence of a catalyst such as fluoboric acid or boron trifluoride and in an organic solvent such as dichloromethane or by reaction of the free or salified 15-hydroxy group with an alkyl or aralkyl halide in presence of a base such as silver oxide and in a solvent such as dimethylsulphoxide and dimethylformamide.

For example, the saponification may be carried out as described above by treatment with a base, such as an alkaline hydroxide, in an aqueous or alcoholic/aqueous solution, as well as the esterification may be performed by treatment with an anhydride or a halide of an acid in the presence of a base or by treatment with a diazoalkane. Thus, the conversion of a compound of formula (I), wherein A is —COOR$_a$, wherein R$_a$ is hydrogen into a compound of formula (I), wherein A is —CONR$_b$R$_c$, wherein R$_b$ and R$_c$ are as defined above, may be effected by treatment with an amine of formula NHR$_b$R$_c$ in the presence of a condensing agent, e.g. a carbodiimide such as dicyclohexylcarbodiimide and the conversion of a compound of formula (I), wherein A is —COOR$_a$, wherein R$_a$ is a C$_1$–C$_{12}$ alkyl group, into a compound of formula (I), wherein A is —CONR$_b$R$_c$, may be performed, e.g., by treatment with an amine of formula NHR$_b$R$_c$ in a suitable organic solvent at the reflux temperature for 2–3 hours.

The lactol of formula (II) may be prepared, in turn, by means of a multi-step process using as starting material an optically active or racemic lactone of formula (VI)

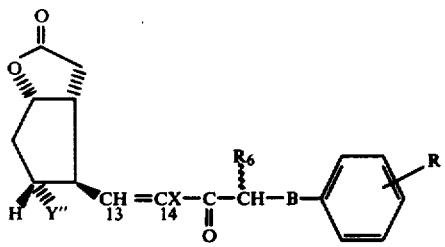

(VI)

wherein Y" is hydroxy, acyloxy or a known protecting group bound to the ring through an ethereal oxygen atom, X, R$_6$, B and R are as defined above, and wherein the hydrogen atom linked to the carbon atom in the 13-position and the halogen atom linked to the carbon atom in the 14-position (prostaglandin numbering) may be either in the trans-position or in the cis-position. The multi-step process to prepared the compound of general formula (II) starting from the lactone of formula (VI) involves the following steps:

(a) reduction of the 15-oxo-group (prostaglandin numbering) of the lactone of formula (VI) to yield a mixture of 15S- and 15R- ols having the formulae (VIIa) and (VIIb):

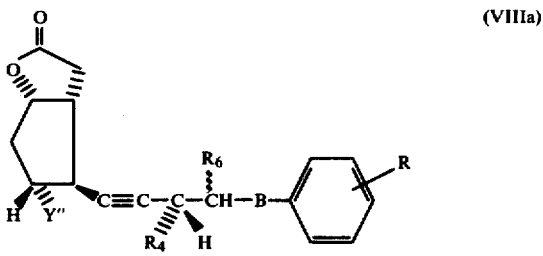

(VIIIa)

wherein R$_4$ is hydroxy, C$_1$–C$_6$ alkoxy or aralkoxy and Y", R$_6$, B and R are as defined above, or a compound of formula (VII Ib)

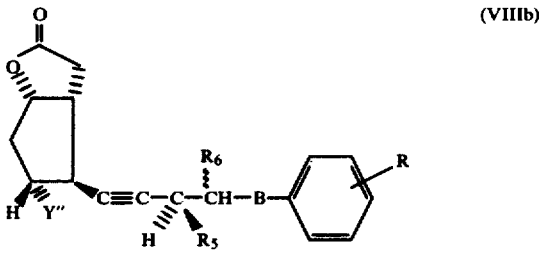

(VIIIb)

wherein R$_5$ is hydroxy, C$_1$–C$_6$ alkoxy or aralkoxy and Y", R$_6$, B and R are as defined above.

If desired, the reduction may follow the dehydrohalogenation. The reduction of the 15-oxo-group may be suitably performed in an organic solvent, such as acetone, diethyl ether, dimethoxyethane, dioxane, or benzene or their mixtures, by using, e.g. metal borohydrides, in particular sodium borohydride, lithium borohydride, zinc borohydride and sodium trimethoxyborohydride.

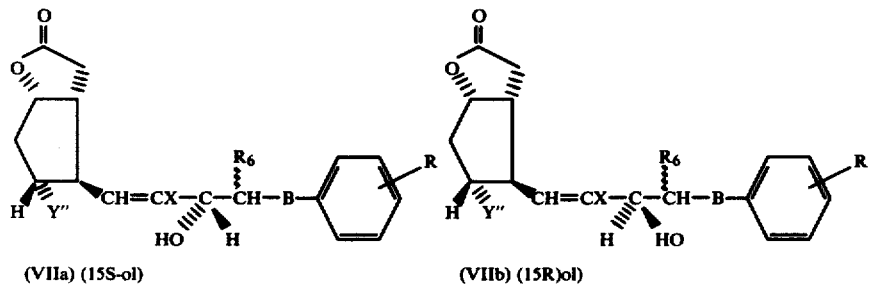

(VIIa) (15S-ol)    (VIIb) (15R)ol)

wherein Y", X, R$_6$, B and R are as defined above, which, when Y" is different from hydroxy, are optionally converted into the corresponding 15S-(C$_1$–C$_6$)-alkoxy or aralkoxy derivatives, e.g., by treatment with a diazoalkane or by reaction with an alkyl or aralkyl halide in the presence of a hydrohalic acid acceptor, followed by the separation of the 15S-compound from the 15R-compound, by the dehydrohalogenation of the separated compounds, to give a compound of formula (VIIIa)

When the etherification of the 15 (S or R)-hydroxy group is carried out by treatment with a diazoalkane, the solvent used is preferably a halogenated hydrocarbon and the reaction is preferably performed in the presence of a catalyst such as borotrifluoride or tetrafluoboric acid (e.g. 0.01 equivalents) with an excess of the diazoalkane. When the etherification is carried out by reaction with an alkyl or aralkyl halide, the solvents used are preferably dimethylsulphoxide, hexamethylphosphoramide, dimethylformamide and the acceptor of the formed hydrohalic acid is a base selected e.g. from the group consisting of barium oxide and silver oxide and an excess of halide is employed. The separation of the 15S-compound from the 15R-compound may be performed by chromatography, e.g. silica gel chromatography, or by fractionated crystallization.

The dehydrohalogenation may be performed in a solvent which is preferably selected from the group consisting of dimethylsulphoxide, dimethylformamide and hexamethylphosphoramide in the presence of a base which may be for example an alkaline metal amide, potassium t.butoxide or the anion $CH_3-SO-CH_2^{(-)}$.

(b) Optional conversion of a compound of formula (IX)

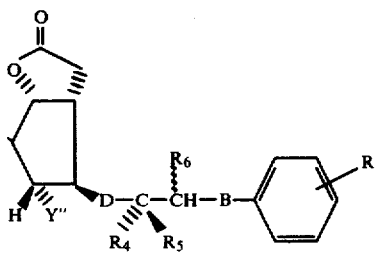

(IX)

wherein Y'', D, $R_4$, $R_5$, $R_6$, B and R are as defined above, into a compound of formula (X)

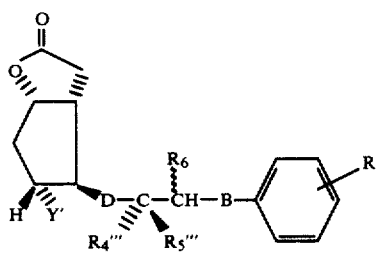

(X)

wherein D, $R_6$, B and R are as defined above, Y' is a known protecting group bound to the ring through an ethereal oxygen atom and one of $R_4'''$ and $R_5'''$ is a known protecting group bound to the chain by an ethereal oxygen atom and the other is hydrogen.

This conversion is preceded, when in the compound of formula (VIII) Y'' is an acyloxy group, by saponification for example by mild treatment with an alkali, to give a compound of formula (VIII) wherein Y'' is hydroxy.

The conversion of a comound of formula (IX) into a compound of formula (X), i.e. the protection of the hydroxy groups in the 11- and/or 15-position by a known protecting group as defined above, is preferably carried out by reaction with an acetalic ether or a vinylic ether, e.g. of formula

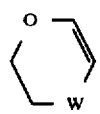

wherein W is —O— or —CH₂—, in the presence of catalytic amounts of e.g. phosphorus oxychloride, p-toluenesulphonic acid or benzenesulphonic acid or with a silyl ether, for instance, by reacting a trisubstituted chlorosilane in the presence of an acceptor base (for example a trialkylamine) of the hydrohalic acid formed or with an enol ether, for instance by reaction, in the presence of an acid catalyst, with a 1,1-dialkoxy-cyclopentane or cyclohexane, at the reflux temperature in an inert solvent and then distilling the alcohol formed to obtain mixed dialkoxy ethers or enol ethers, according to the amount of catalyst used or the heating time.

(c) Reduction of a compound of formula (XI)

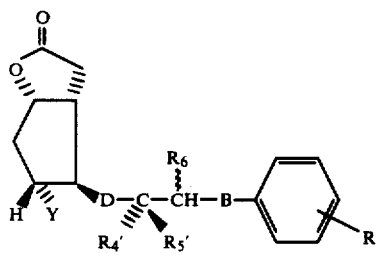

(XI)

wherein D, B, $R'_4$, $R'_5$, $R_6$, R and Y are as defined above, to give the lactol of formula (II).

The reduction may be performed by treatment with diisobutylaluminium hydride or sodium bis-(2-methoxyethoxy)-aluminium hydride in an inert solvent, for example, toluene, n-heptane, n-hexane or benzene or their mixtures, at below 30° C. All the compounds mentioned under items (a), (b) and (c), may be either optically active compounds or racemic mixtures thereof.

The lactone of formula (VI) may be in turn prepared in an only one step by reaction of an aldehyde of formula (XII)

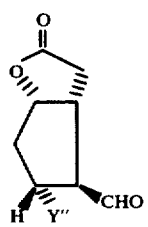

(XII)

wherein Y'' is as defined above, with a halo-phosphonate carbanion of formula (XIII)

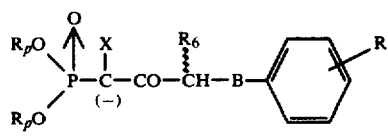

(XIII)

wherein $R_p$ is lower alkyl and X, $R_6$, B and R are as defined above.

The reaction is suitably performed in a solvent which is preferably dry benzene, dimethoxyethane, tetrahydrofuran, dimethylformamide or their mixtures, and using a suspension of 1.1–1.2 molar equivalent of the halo-phosphonate carbanion.

When in the aldehyde of formula (XII) Y'' is an acyloxy group, it may be for example, acetoxy, propionyloxy, benzoyloxy and p-phenyl-benzoyloxy. When Y'' is a known protecting group bound to the ring through an ethereal oxygen atom, it may be for example one of the ethereal protecting groups reported hereabove. The aldehyde of formula (XII) may be prepared substantially as described by E. J. Corey at al., Ann. of New York Acad. of Sciences, 180, 24 (1971).

The halo-phosphonate carbanion of formula (XIII) may be in turn prepared by reacting a halo-phosphonate of formula (XIV)

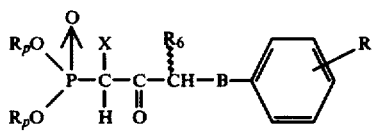

(XIV)

wherein $R_p$, X, $R_6$, B and R are as defined above, with an equivalent of a base preferably selected from the group consisting of sodium hydride, lithium hydride, calcium hydride, an alkyl-lithium derivative and the anion $CH_3$—$SO$—$CH_2^{(-)}$.

The halo-phosphonate of formula (XIV) may be obtained by halogenation of a phosphonate of formula (XV)

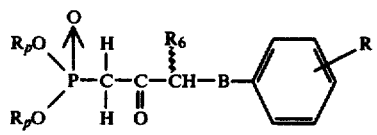

(XV)

wherein $R_p$, B, $R_6$, and R are as defined above.

The halogenation may be carried out in a conventional manner, operating substantially as in the halogenation of β-ketoesters.

The phosphonate of formula (XV) may be prepared by known methods, e.g. according to E. J. Corey et al., J. Am. Chem. Soc. 90, 3247 (1968) and E. J. Corey and G. K. Kwiatkowsky, J. Am. Chem. Soc., 88, 5654 (1966). Preferably the phosphonate of formula (XV) is prepared by reaction of lithium methylphosphonate with a lower alkyl ester of the acid of formula

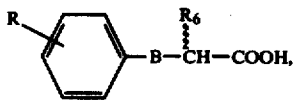

wherein R, B and $R_6$ are as defined above.

When this acid contains asymmetric carbon atoms, it is possible to use either the racemic acid or one of its optical antipodes. Also the halides of the above acid, e.g. the chlorides, may be used in the reaction with lithium methylphosphonate.

The above mentioned acid as well as its lower alkyl esters and its halides, is a known compound or may be prepared by known methods.

For example β-phenyl-propionic acid and β-phenyl-α-alkyl-propionic aicds may be prepared starting from a benzyl halide or a substituted benzyl halide by malonic synthesis; phenoxy-aliphatic acids may be obtained by etherification of an optionally substituted phenol by reaction with a halo-substituted aliphatic acid; benzyloxy-aliphatic acids may be prepared by etherification of the hydroxy groups of an hydroxy-aliphatic acid by reaction e.g. with a benzyl halide.

Alternatively, the halo-phosphonate carbanion of formula (XIII) may be prepared by reacting a phosphonate carbanion of formula (XVI)

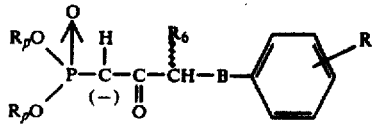

(XVI)

wherein $R_p$, B, $R_6$ and R are as defined above, with a halogenating agent selected from the group consisting of $Br_2$, pyrrolidone-hydrotribromide (PHTB), dioxandibromide, N-chloroacetamide, N-chlorosuccinimide, N-bromosuccinimide, N-bromoacetamide, N-bromocaprolactame, N-iodosuccinimide.

By using the imides as halogenating agents, the carbanion of the halo-phosphonate of formula (XIII) is obtained directly with the use of only one equivalent of base; otherwise, it should be necessary to use another equivalent of a base to obtain the carbanion of the halophosphonate.

The phosphonate carbanion of formula (XVI) may be in turn obtained by the treatment of the phosphonate of formula (XV) with an equivalent of a base, e.g. sodium, lithium or calcium hydride.

The halo-lactone of formula (VI) wherein X is bromine, may also be obtained by a multi-step process starting from a lactone of formula (XVII)

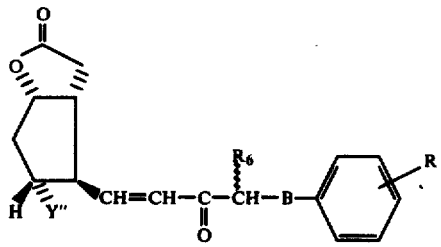

(XVII)

wherein Y″, B, $R_6$ and R are as defined above, which may be prepared substantially as described by E. J. Corey et al., Annals of New York Acad. of Science, 180, 24 (1971). This multi-step process involves the following steps:

(a′) reduction of the lactone of formula (XVII) to give a mixture of the 15S- and 15R-ols of formulae (XVIIIa) and (XVIIIb)

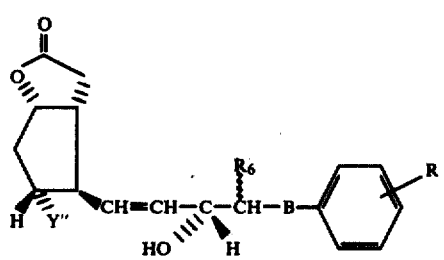

(XVIIIa)

(15S-ol)

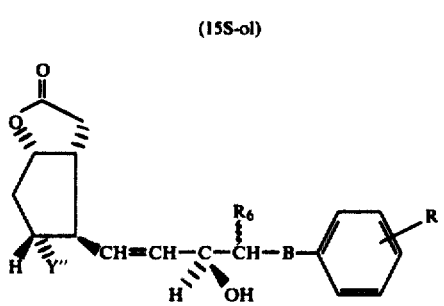

(XVIIIb)

(15R-ol)

wherein Y″, B, $R_6$ and R are as defined above. The reduction may be performed in an organic solvent, such as acetone, diethylether and dimethoxyethane, by using, for example, sodium borohydride, zinc borohydride, and lithium borohydride.

(b') halogenation of the mixture of the two 15R- and 15S-ols to give a mixture of 13ξ,14ξ-dibromoalcohols of formulae (XIXa) and (XIXb)

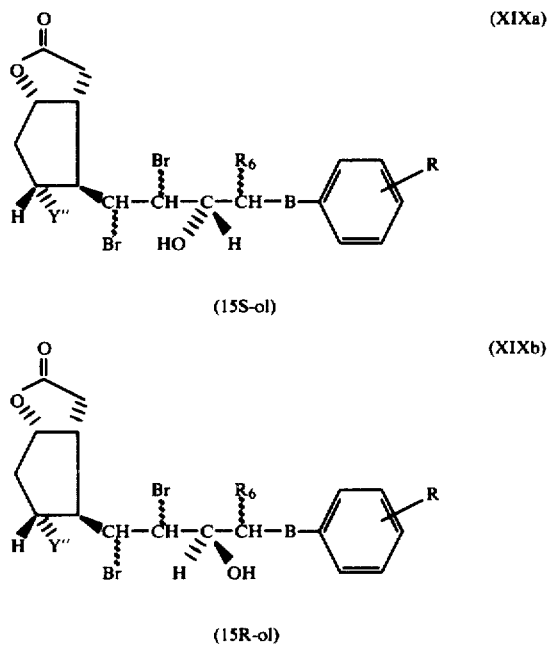

wherein Y', B, $R_6$ and R are as defined above.

The halogenation is carried out in an inert solvent, preferably selected from the group consisting of halogenated solvent, e.g. dichloromethane, dichlorethane, $CCl_4$ and a linear or cyclic ether, e.g. tetrahydrofuran, dioxane, dimethoxyethane or their mixtures, using a molar equivalent of halogenating agent or an excess of the same agent, which may be, e.g. $Br_2$, dioxandibromide, pyrrolidone hydrotribromide.

(c') oxidation of the mixture of the 13ξ, 14ξ-dibromoalcohols to give a 13ξ, 14ξ-dibromo-15-oxo-derivative of formula (XX)

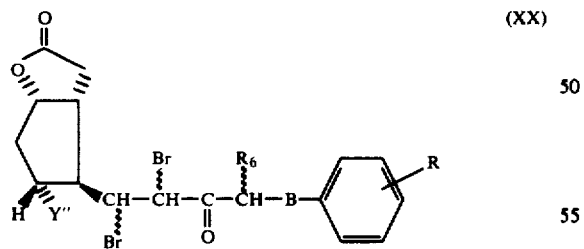

wherein Y", B, $R_6$ and R are as defined above.

The oxidation is carried out at a temperature ranging between −25° and the room temperature, by using a dichloromethane solution of the pyridine-chromic anhydride complex or a sulphoric solution of chromic anhydride in acetone (Jones reagent), or a carbodiimide, working in dimethylsulphoxide in presence of a suitable acid.

(d') dehydrohalogenation of the 13ξ,14ξ-dibromo-15-oxo-derivative to give the halo-lactone of formula (VI) wherein X is bromine.

The dehydrohalogenation may be performed by using an organic base, for example a tert.amine in an inert solvent, or alternatively by using an inorganic base, for example potassium acetate in a solvent such as methanol, ethanol acetic acid and the like. A further alternative process for the preparation of the halo lactone of formula (VI) wherein X is bromine, is the reaction of the lactone of formula (XVII), in an ethereal anhydrous solvent such as tetrahydrofuran and dimethoxyethane or in a halogenated hydrocarbons with a halogenating agent such as bromine, phenyltrimethylammoniumtribromide and in particular pyrrolidone-hydrotribromide (1.1–1.3 molar equivalent) to give directly the 13ξ,14ξ-dibromo-15-oxo-derivative of formula (XX) which is then dehydrohalogenated as above described, to give the halo-lactone of formula (VI), wherein X is bromine. When acetic acid is used as solvent, the reaction may be performed in one step without recovering the intermediate dibromo compounds of formula (XX) by treatment of the reaction mixture (after addition of bromine), with about 1.1–2.5 molar equivalent of anhydrous potassium carbonate.

Also in the alternative methods for the preparation of the halo-lactone of formula (VI), all the compounds may be either optically active compounds or racemic mixtures thereof. In the preparation of the halo-lactone of formula (VI) according to the here-above described methods, both compounds wherein the hydrogen atom linked to the carbon atom in the 13- position and the halogen atom linked to the carbon atom in the 14- position (prostaglandin numbering) are in the trans-position (geometric trans-isomers) and compounds wherein said atoms are in the cis-position (geometric cis-isomers) are obtained.

The geometric trans-isomers are obtained in a far higher percentage (92–95%), while the geometric cis-isomers are obtained in a far lower percentage (5–8%).

The geometric trans-isomers of formula

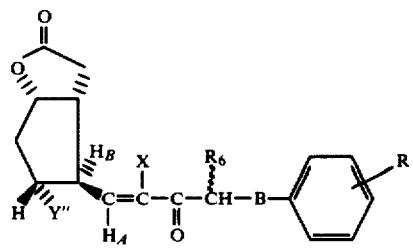

can be easily distinguished from the geometric cis-isomers of formula

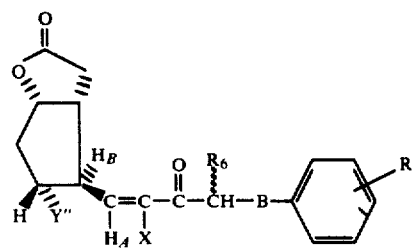

in that the $H_A$ vinylic protons of the two isomers resonate at different positions and the coupling constants of the $H_A$ vinylic proton with the $H_B$ proton are well different (respectively 9 Hz for the trans-isomer and 10.2 Hz for the cis-isomer).

Anyway, both the trans-isomers and the cis-isomers are intermediates for the synthesis of the 13,14-dehydro-prostaglandins of the invention.

The lactol of formula (II) wherein D is —C≡C— may be also prepared by dehydrohalogenation of the lactol of formula (II) wherein D is —CH=CX—, wherein X is bromine, chlorine or iodine. The dehydrohalogenation may be carried out in an aprotic solvent preferably selected from the group consisting of dimethylsulphoxide, dimethylformamide and hexamethylphosphoramide by treatment with a base preferably selected from the group consisting of potassium tert.butylate, an alkali metal amide and the anion $CH_3—SO—CH_2^{(-)}$.

Among the intermediates described in this specification, the following are compounds of the invention:

(1) the halo-phosphonate carbanion of formula (XIII);

(2) the lactol of formula (II);

(3) the lactone of formula (XXI)

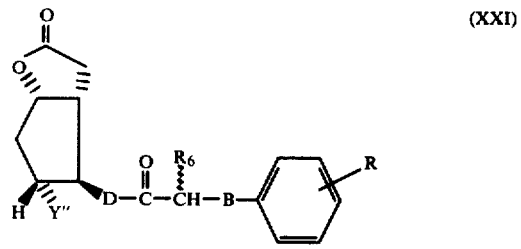
(XXI)

wherein Y'', D, $R_6$, B and R are as defined above;

(4) a compound of formula (XXII)

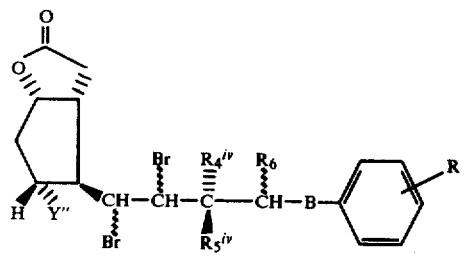
(XXII)

wherein Y'', $R_6$, B and R are as defined above, and one of $R_4^{IV}$ and $R_5^{IV}$ is hydroxy and the other is hydrogen, or $R_4^{IV}$ and $R_5^{IV}$ together form an oxo group;

(5) a compound of formula (XXIII)

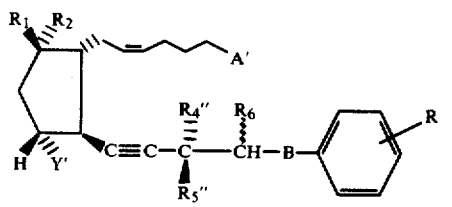
(XXIII)

wherein A', Y', R''$_4$, R''$_5$, $R_6$, B and R are as defined above, one of $R_1$ and $R_2$ is hydrogen and the other is 60 hydroxy or acyloxy or $R_1$ and $R_2$ togehter form an oxo group.

All the intermediates mentioned under the foregoing points (1) to (5) are optically active or racemic compounds.

The compounds of formula (I) may be used for the same therapeutical indications as natural prostaglandins, with respect to which, however, they offer the advantage of being no substrates for the enzyme 15-prostaglandin dehydrogenase, which as is known, quickly inactivates natural prostaglandins, and, moreover, are characterized by a more selective therapeutical action.

The compounds of formula (I) furthermore inhibit the use of natural prostaglandins as substrate by the same enzyme. Using the 15-hydroxy-prostaglandin-dehydrogenase drawn from human placenta, in vitro tests carried out with for example 13,14-dehydro-17-phenyl-20,19,18-trinor-$PGF_{2\alpha}$(or 5c-9α,11α,15S-trihydroxy-20,19,18-trinor-17-phenyl-prost-5-en-13-ynoic acid), showed that the inhibition becomes partially competitive with respect to $PGF_{2\alpha}(K_i=130\ \mu M)$.

Because of their biological responses, the compounds of the invention are useful to study, prevent, control, or alleviate a wide variety of dieases and undesirable physiological conditions in birds and mammals, including humans, useful domestic animals and zoological specimens, and in laboratory animals, for example mice, rats, rabbits and monkeys.

In particular the compounds of the invention have selective luteolytic, abortifacient and labor-inducing activity and extremely low undesired gastro-intestinal effects.

The following Table shows the comparison of two compounds of the present invention, i.e. 13,14-dehydro-17-phenyl-20,19,18-trinor-$PGF_{2\alpha}$ and 13,14-dehydro-15S-methoxy-17-phenyl-20,19,18-trinor-$PGF_{2\alpha}$ (5c-9α,11α-dihydroxy-15S-methoxy-20,19,18-trinor-17-phenyl-prost-5-en-13-ynoic acid), with $PGF_{2\alpha}$,13,14-dehydro-$PGF_{2\alpha}$, and with the olefinic analogue 5c,13t-9α,11α,15S-trihydroxy-20,19,18-trinor-17-phenyl-prosta-5,13-dienoic acid (or 17-phenyl-20,19,18-trinor-$PGF_{2\alpha}$) in the following in vitro tests: guinea pig ileum test and rat uterus test. In the Table the conventional value of 1 was given to the activity of $PGF_{2\alpha}$ in both tests.

TABLE

| Compound | Guinea Pig Ileum* | Rat Uterus** |
|---|---|---|
| $PGF_{2\alpha}$ | 1 | 1 |
| 17-phenyl-20,19,18-trinor-$PGF_{2\alpha}$ | 2.34 (1.47–3.72) | 1.54 (0.73–3.23) |
| 13,14-dehydro-$PGF_{2\alpha}$ | 0.6 (0.406–0.913) | 1.09 (0.66–1.77) |
| 13,14-dehydro-17-phenyl-20,19,18-trinor-$PGF_{2\alpha}$ | 0.6 (0.29–1.23) | 22.74 (16.05–32.2) |
| 13,14-dehydro-15S-methoxy-17-phenyl-20,19,18-trinor-$PGF_{2\alpha}$ | 0.05 (0.01–0.17) | 4.4 (3.12–6.21) |

*In a 10 ml thermostatic bath held at 35° C., ilea of male guinea pigs, under 0.5 g traction, were subjected to carbon-dioxide in a Tyrode solution; the preparation was left for 30 minutes to stabilize before the compounds were tested. The response was recorded using a isotonic frontal lever, long enough to amplify the response 4.5 times.

**In a 10 ml thermostatic bath held at 29° C., oestrogenized rat uteri under 0.5 g traction were subjected to carbon-dioxide in a Dejalon saline solution. The prepration was left to stabilize for 30 minutes before the compounds were tested. Response was measured using a isotonic frontal lever, long enough to amplify the response 4.5 times.

From the comparison of the activities in the above in vitro tests it is evident that a remarkable increase of the action selectivity on miometrium was obtained as well as a reduced effect on the muscle of the gastroenteric apparatus was recorded, that means, a reduction of the gastrointestinal side effects which are always present when natural prostaglandins are administered.

Also the phenoxy derivatives, e.g. 13,14-dehydro-16-m-trifluoromethylphenoxy-20,19,18,17-tetranor-PGF$_{2\alpha}$ (or 5c-9α,11α,15S-trihydroxy-20,19,18,17-tetranor-16-m-trifluoromethylphenoxy-prost-5-en-13-ynoic acid) and 13,14-dehydro-16-p-fluorophenoxy-20,19,18,17-tetranor-PGF$_{2\alpha}$ (or 5c-9α,11α,15S-trihydroxy-20,19,18,17-tetranor-16-p-fluorophenoxy-prost-5-en-13-ynoic acid), when compared with PGF$_{2\alpha}$ (to whose activity the conventional value of 1 was given), show a very high activity in the rat uterus test, i.e. 3.86 (2.96–5.03) and, respectively, 1.91 (1.34–2.73) and a very low activity in the guinea pig ileum test: 0.50 (0.05–5) for both the compounds.

The action selectivity of the compounds of the invention on the miometrium and on the reproductive apparatus is also proven by the remarkable increase of the luteolytic activity in the pregnant rat at the 9th–10th day of pregnancy. In fact, if the conventional value 1 is given to the luteolytic activity of PGF$_{2\alpha}$, the value of 100 at least is to be given to the luteolytic activity of 13,14-dehydro-17-phenyl-20,19,18-trinor-PGF$_{2\alpha}$, and the value of 200 to the luteolytic activity of 13,14-dehydro-16-p-fluorophenoxy-20,19,18,17-tetranor-PGF$_{2\alpha}$.

Pharmaceutical compositions containing a solution of 13,14-dehydro-17-phenyl-20,19,18-trinor-PGF$_{2\alpha}$ as sodium salt or 13,14-dehydro-16-p-fluorophenoxy-20,19,18,17-tetranor-PGF$_{2\alpha}$ as sodium salt in an aqueous isotonic buffered (pH 7.5) medium at a concentration of 0.5 mg/ml were tested as to their ability of synchronizing the estrum of mares, cows, heifers and sowes and in all cases very good results were obtained. After administration of 0.5–3 ml of the above solution it was noted a pronounced downfall of the haematic levels of progesterone which indicates a high luteolytic activity.

Furthermore, the compounds of formula (I), and in particular the PGF$_{2\alpha}$ derivatives, e.g. 13,14-dehydro-17-phenyl-20,19,18-trinor-PGF$_{2\alpha}$, own a utero-kinetic, i.e. abortifacient and labor-inducing, activity higher than that of the corresponding cycloalkyl derivatives, e.g. 13,14-dehydro-17-cyclohexyl-20,19,18-trinor-PGF$_{2\alpha}$, as shown by the following test:

Female rabbits of the average weight of four kilograms, ovariectomized one week before, were anesthetized with pentobarbital sodium (40 mg/kg i.v.) and then a catheter bearing a rubber balloon filled with water was inserted into an uterine horn, through the vaginal opening, and uterine motility was recorded by means of a pressure transducer (Statham P 23 ID) connected to a Beckman R 411 recorder; the tested prostaglandins were then administered intravenously, each animal serving for one dose, in order to avoid tachyphylaxis.

Dose-response curves were obtained for each compound: the PGF$_{2\alpha}$ compounds of the invention, e.g. 13,14-dehydro-17-phenyl-20,19,18-trinor-PGF$_{2\alpha}$, resulted about 10 to 15 times more potent than the corresponding cycloalkyl derivatives, e.g. 13,14-dehydro-17-cyclohexyl-20,19,18-trinor-PGF$_{2\alpha}$. The compounds of the invention, and in particular the PGF$_{2\alpha}$ derivatives, are therefore useful for controlling the reproductive cycle in ovulating female mammals, including humans and animals such as cattle, monkeys, rats, rabbits, dogs and the like. For this purpose, the compounds of the invention are administered during a span of time starting approximately at the time of ovulation and ending approximately at the time of menses or just prior to menses. Additionally, expulsion of an embryo or a fetus is accomplished by administration of the compound during the first third of the normal mammalian gestation period.

The 9-oxo-derivatives (PGE analogues) of formula (I), when compared with PGE$_2$ according to the method described by H. Shay et al., Gastroenter., 26,906 (1954) are about 2 times more active as gastric antisecretory agents than PGE$_2$ and therefore are useful to reduce and control excessive gastric secretion, thereby reducing or avoiding gastrointestinal ulcer formation and accelerating the healing of such ulcers already present in the gastrointestinal tract.

Moreover, the antisecretory activity of the 9-oxo-compounds of formula (I), wherein a lower alkyl, particularly a methyl, is present on the carbon atom in the 16-position, is further increased of 2 times when the alkyl is a 16S-alkyl, and of 4 times when the alkyl is a 16R-alkyl.

The compounds of the invention may be administered, either to humans or to animals, in a variety of dosage forms, e.g. orally in the form of tablets, capsules or liquids; rectally in the form of suppositories, parenterally, subcutaneously or intramuscularly, with intravenous administration being preferred in emergency situations; by inhalation in the form of aerosols or solutions for nebulizers; in the form of sterile implants for prolonged action; or intravaginally in the form e.g. of bougies.

The pharmaceutical or veterinary compositions containing the compounds of the invention are prepared in a conventional way and contain conventional carriers and/or diluents.

For example, for intravenous injection or infusion, sterile aqueous isotonic solutions are preferred. For subcutaneous or intramuscular injection, sterile solutions or suspensions in aqueous or non-aqueous media are used; for tissue implants, a sterile tablet or silicone rubber capsule containing or impregnated with the substance is used.

Conventional carriers or diluents are for example water, gelatine, lactose, starches, magnesium stearate, talc, vegetable oils, cellulose and the like.

Doses in the range of about 0.01 to 5 mg per kg of body weight may be used 1 to 4 times a day, the exact dose depending on the age, weight and condition of the subject to be treated and on the frequency and route of administration. For example, the compounds of the invention can be administered by intravenous infusion of a sterile isotonic saline solution at the rate of 0.01 to 10, preferably 0.05 to 1, μg/kg of mammal body weight per minute.

The invention is illustrated by the following examples, wherein the abbreviations "THP", "DIOX", "DMSO", "THF", "DMF", "DIBA", and "Et$_2$O" refer to tetrahydropyranyl, dioxanyl, dimethylsulphoxide, tetrahydrofuran, dimethylformamide, diisobutylaluminium hydride and ethyl ether, respectively.

EXAMPLE 1

To a stirred solution of NaH (80% dispersion in mineral oil, 1.67 g) in dry benzene (300 ml) was added a dimethyl (2-oxo-4-phenyl)-butyl-phosphonate (14.60 g) solution in dry benzene (30 ml). After one hour the vigorously stirred mixture was cooled at 5°–8° C., treated with finely powdered N-bromo succinimide (9.28 g) and then, after 15 minutes, with a benzene (50 ml) solution of 5β-formyl-2α,4α-dihydroxy-cyclopent-1-yl-acetic acid-γ-lactone-4-p-phenylbenzoate (12.9 g).

The stirring was continued for 90 minutes, then the reaction mixture was treated with aqueous 20% NaH$_2$PO$_4$ solution, the organic phase was separated, washed with water and dried. After removal of solvents in vacuum, crystallization from ethyl/ether afforded 5β(2'-bromo-3'-oxo-5'-phenyl-pent-1'-trans-1'-enyl)-2α,4α-dihydroxy-cyclopentane-1α-acetic acid-γ-lactone-4-p-phenylbenzoate (17.6 g), m.p. 134°–140° C. [α]$_D$=−103° [α]$_{365}$=−462° (C=0.5%, CHCl$_3$). Starting from a 4-acetate, the corresponding 4-acetate was obtained.

EXAMPLE 2

5β(3'-oxo-4'-(m-trifluoromethyl)-phenoxy-but-1'-trans-1'-enyl)-2α,4α-dihydroxy-cyclopentane-1α-acetic acid-γ-lactone-4-p-phenylbenzoate (5.05 g; m.p. 114°–115° C.) was obtained starting from 5β-formyl-2α,4α-dihydroxy-cyclopentane-1α-acetic acid-γ-lactone-4-p-phenylbenzoate (5.9 g) in THF (70 ml) by treatment with a suspension of sodium salt of dimethyl-(2-oxo-3-(m-trifluoromethyl)-phenoxypropylphosphonate (7.12 g; NaH 80% 0.60 g) in THF (180 ml). A bromine (1.52 g) solution in acetic acid (5 ml) was added, dropwise, to a stirred solution of the above mentioned 3'-oxo-compound (4.95 g) in acetic acid (10 ml) to obtain persistent feeble red colour, then the solution of crude, not isolated, 5β-(1'≷,2'≷-dibromo-3'-oxo-4'-(m-trifluoromethyl)-phenoxy-but-1'-trans-1'-enyl)-2α,4α-dihydroxy-cyclopentane-1α-acetic acid-γ-lactone-4-p-phenylbenzoate was treated with anhydrous K$_2$CO$_3$ (3.2 g) and heated for 3 hours at 80° C. After cooling at room temperature a precipitate of crystalline material was obtained. It was filtered and dissolved with methylene chloride. The organic phase was washed with 10% NaHCO$_3$ aqueous solution and water until neutral, affording by removal of solvent and crystallization (from ethyl ether): 5β-(2'-bromo-3'-oxo-4'-(m-trifluoromethyl)-phenoxy-but-1'-trans-1'-enyl)-2α,4α-dihydroxy-cyclopentane-1α-acetic acid-γ-lactone-4-p-phenylbenzoate, m.p. 108°–110°.

EXAMPLE 3

5β-(3'-oxo-5'-phenyl-pent-1'-trans-1'-enyl)-2α,4α-dihydroxy-cyclopentane-1α-acetic acid-γ-lactone-4-p-phenylbenzoate (4.3 g, m.p. 127°–128° C. [α]$_D$=−135° [α]$_{365°}$=−595 (C=0.5% CHCl$_3$) was obtained by treatment of benzene (70 ml) solution of 5β-formyl-2α,4α-dihydroxy-cyclopentane-1α-acetic acid-γ-lactone-4-p-phenylbenzoate (3.5 g) with a sodium salt suspension in benzene (70 ml) of the phosphonate prepared starting from NaH (0.45 g) (80% dispersion in mineral oil) and dimethyl-(2-oxo-4-phenyl)-butyl-phophonate (3.93 g). The reaction mixture was stirred for 90 minutes at room temperature, treated with an excess of aqueous 20% NaH$_2$PO$_4$ solution and then the organic phase was separated, washed until neutral, affording after cystallization from methanol the α,β-unsaturated ketone.

EXAMPLE 4

Using in the procedure of Example 1 a phosphonate selected from the group consisting of:
dimethyl-[2-oxo-4-(4'-fluoro)-phenyl]-butyl-phosphonate;
dimethyl-(2-oxo-4-(3'-chloro)-phenyl)-butyl-phosphonate;
dimethyl-[2-oxo-4-(3'-trifluoromethyl)-phenyl]-butyl-phosphonate;
dimethyl-[2-oxo-4-(4'-methoxy)-phenyl]-butyl-phosphonate;
dimethyl-(2-oxo-3-phenyl)-propyl-phosphonate;
dimethyl-(2-oxo-5-phenyl)-pentyl-phosphonate;
dimethyl-(2-oxo-3S-methyl-4-phenyl)-butyl-phosphonate;
dimethyl-(2-oxo-3R-methyl-4-phenyl)-butyl-phosphonate;
dimethyl-(2-oxo-3S-methyl-3-phenoxy)-propyl-phosphonate;
dimethyl-(2-oxo-3R-methyl-3-phenoxy)-propyl-phosphonate;
dimethyl-(2-oxo-3-phenoxy)-propyl-phosphonate;
dimethyl-(2-oxo-3-benzyloxy)-propyl-phosphonate;
dimethyl-[2-oxo-3-(4'-methoxy)-phenoxy]-propyl-phosphonate;
dimethyl-[2-oxo-3-(3'-chloro)-phenoxy]-propyl-phosphonate;
dimethyl-[2-oxo-3-(4'-fluoro)-phenoxy]-propyl-phosphonate;
dimethyl-[2-oxo-3-(3'-trifluoromethyl)-phenoxy]-propyl-phosphonate, the following 2α,4α-dihydroxy-cyclopentane-1α-acetic acid-γ-lactone-4-p-phenylbenzoate derivatives were prepared:

5β-[2'-bromo-3'-oxo-5'-(4"-fluoro)-phenyl-pent-1'-trans-1'-enyl]-;
5β-[2'-bromo-3'-oxo-5'-(3"-chloro)-phenyl-pent-1'-trans-1'-enyl]-;
5β-[2'-bromo-3'-oxo-5'-(3"-trifluoromethyl)-phenyl-pent-1'-trans-1'-enyl]-;
5β-[2'-bromo-3'-oxo-5'-(4"-methoxy)-phenyl-pent-1'-trans-1'-enyl]-;
5β-(2'-bromo-3'-oxo-4'-phenyl-but-1'-trans-1'-enyl)-;
5β-(2'-bromo-3'-oxo-6'-phenyl-hex-1'-trans-1'-enyl)-;
5β-(2'-bromo-3'-oxo-4'S-methyl-5'-phenyl-pent-1'-trans-1'-enyl)-;
5β-(2'-bromo-3'-oxo-4'R-methyl-5'-phenyl-pent-1'-trans-1'-enyl)-;
5β-(2'-bromo-3'-oxo-4'S-methyl-4'-phenoxy-but-1'-trans-1'-enyl)-;
5β-(2'-bromo-3'-oxo-4'R-methyl-4'-phenoxy-but-1'-trans-1'-enyl)-;
5β-(2'-bromo-3'-oxo-4'-phenoxy-but-1'-trans-1'-enyl)-;
5β-(2'-bromo-3'-oxo-4'-benzyloxy-but-1'-trans-1'-enyl)-;
5β-[2'-bromo-3'-oxo-4'-(4"-methoxy)-phenoxy-but-1'-trans-1'-enyl]-;
5β-[2'-bromo-3'-oxo-4'-(3"-chloro)-phenoxy-but-1'-trans-1'-enyl]-;
5β-[2'-bromo-3'-oxo-4'-(4"-fluoro)-phenoxy-but-1'-trans-1'-enyl]-;
5β-[2'-bromo-3'-oxo-4'-(3"-trifluoromethyl)-phenoxy-but-1'-trans-1'-enyl]-.

EXAMPLE 5

Using in the procedure of Example 3 a dimethylphosphonate selected from the group consisting of:
dimethyl-[2-oxo-4-(4'-fluoro)-phenyl]-butyl-phosphonate;
dimethyl-(2-oxo-4-(3'-chloro)-phenyl)-butyl-phosphonate;
dimethyl-[2-oxo-4-(3'-trifluoromethyl)-phenyl]-butyl-phosphonate;
dimethyl-[2-oxo-4-(4'-methoxy)-phenyl]-butyl-phosphonate;
dimethyl-(2-oxo-3-phenyl)-propyl-phosphonate;
dimethyl-(2-oxo-5-phenyl)-pentyl-phosphonate;

dimethyl-(2-oxo-3S-methyl-4-phenyl)-butyl-phosphonate;
dimethyl-(2-oxo-3R-methyl-4-phenyl)-butyl-phosphonate;
dimethyl-(2-oxo-3S-methyl-3-phenoxy)-propyl-phosphonate;
dimethyl-(2-oxo-3R-methyl-3-phenoxy)-propyl-phosphonate;
dimethyl-(2-oxo-3-phenoxy)-propyl-phosphonate;
dimethyl-(2-oxo-3-benzyloxy)-propyl-phosphonate;
dimethyl-[2-oxo-3-(4'-methoxy)-phenoxy]-propyl-phosphonate;
dimethyl-[2-oxo-3-(3'-chloro)-phenoxy]-propyl-phosphonate;
dimethyl-[2-oxo-3-(4'-fluoro)-phenoxy]-propyl-phosphonate;
dimethyl-[2-oxo-3-(3'-trifluoromethyl)-phenoxy]-propyl-phosphonate,
the following 2α,4α-dihydroxy-cyclopentane-1α-acetic acid-γ-lactone-4-p-phenylbenzoate derivatives were obtained:
5β-[3'-oxo-5'-(4''-fluoro)-phenyl-pent-1'-trans-1'-enyl]-;
5β-[3'-oxo-5'-(3''-chloro)-phenyl-pent-1'trans-14-enyl]-;
5β-[3'-oxo-5'-(3''-trifluoromethyl)-phenyl-pent-1'-trans-1'-enyl]-;
5β-[3'-oxo-5'-(4''-methoxy)-phenyl-pent-1'-trans-1'-enyl]-;
5β-(3'-oxo-4'-phenyl-but-1'-trans-1'-enyl)-;
5β-(3'-oxo-6'-phenyl-hex-1'-trans-1'-enyl)-;
5β-(3'-oxo-4'S-methyl-5'-phenyl-pent-1'trans-1'-enyl)-;
5β-(3'-oxo--4'R-methyl-5'-phenyl-pent-1'-trans-1'-enyl)-;
5β-(3'-oxo-4'S-methyl-4'-phenoxy-but-1'-trans-1'-enyl)-;
5β-(3'-oxo-4'R-methyl-4'-phenoxy-but-1'-trans-1'-enyl)-;
5β-(3'-oxo-4'-phenoxy-but-1'-trans-1'-enyl)-;
5β-(3'-oxo-4'-benzyloxy-but-1'-trans-1'-enyl)-;
5β-[3'-oxo-4'-(4''-methoxy)-phenoxy--but-1'-trans-1'-enyl]-;
5β-[3'-oxo-4'-(3''-chloro)-phenoxy-but-1'-trans-1'-enyl]-;
5β-[3'-oxo-4'-(4''-fluoro)-phenoxy-but-1'-trans-1'-enyl]-;
5β-[3'-4'-(3''-trifluoromethyl)-phenoxy-but-1'-trans-1'-enyl]-;
each of these compounds was reacted with bromine in acetic acid and then dehydrohalogenated with anhydrous potassium carbonate using the procedure of Example 2 to obtain the following:
2α,4α-dihydroxy-cyclopentane-1α-acetic acid-γ-lactone-4-p-phenylbenzoate derivatives
5β-[2'-bromo-3'-oxo-5'-(4''-fluoro)-phenyl-pent-1'-trans-1'-enyl]-;
5β-[2'-bromo-3'-oxo-5'-(3''-chloro)-phenyl-pent-1'-trans-1'-enyl]-;
5β-[2'-bromo-3'-oxo-5'-(3''-trifluoromethyl)-phenyl-pent-1'-trans-1'-enyl]-;
5β-[2'-bromo-3'-oxo-5'-(4''-methoxy)-phenyl-pent-1'-trans-1'-enyl]-;
5β-(2'-bromo-3'-oxo-4'-phenyl-but-1'-trans-1'-enyl)-;
5β-(2'-bromo-3'-oxo-6'-phenyl-hex-1'-trans-1'-enyl)-;
5β-(2'-bromo-3'-oxo-4'S-methyl-5'-phenyl-pent-1'-trans-1'-enyl)-;
5β-(2'-bromo-3'-oxo-4'R-methyl-5'-phenyl-pent-1'-trans-1'-enyl)-;
5β-(2'-bromo-3'-oxo-4'S-methyl-4'-phenoxy-but-1'-trans-1'-enyl)-;
5β-(2'-bromo-3'-oxo-4'R-methyl-4'-phenoxy-but-1'-trans-1'-enyl)-;
5β-(2'-bromo-3'-oxo-4'-phenoxy-but-1'-trans-1'-enyl)-;
5β-(2'-bromo-3'-oxo-4'-benzyloxy-but-1'trans-1'-enyl)-;
5β-[2'-bromo-3'-oxo-4'(4''-methoxy)-phenoxy-but-1'-trans-1'-enyl]-;
5β-[2'-bromo-3'-oxo-4'-(3''-chloro)-phenoxy-but-1'-trans-1'-enyl]-;
5β-[2'-bromo-3'-oxo-4'-)4''-fluoro)-phenoxy-but-1'-trans-1'-enyl]-;
5β-[2'-bromo-3'-oxo-4'-(3''-trifluoromethyl)-phenoxy-but-1'-trans-1'-enyl]-;

EXAMPLE 6

3% bromine solution (30 ml) in carbon tetrachloride was added to a solution of 5β-(3'-oxo-5'-phenyl-pent-1'-trans-1'-enyl)-2α,4α-dihydroxy-cyclopentane-1α-acetic acid-γ-lactone-4-p-phenylbenzoate in carbon tetrachloride (150 ml). After discoloration, the reaction mixture was treated with pyridine (10 ml) and stirred at room temperature for 10 hours.

The organic layer was washed with 4N aqueous sulfuric acid and water until neutral, dried and then the solvents were evaporated in vacuum. The residue was crystallized from ethyl ether to afford 5β-(2'-bromo-3'-oxo-5'-phenyl-pent-1'-trans-1'-enyl)-2α,4α-dihydroxy-cyclopentane-1α-acetic acid-γ-lactone-4-p-phenylbenzoate, m.p. 139°-140° C.

EXAMPLE 7

To a solution of 2.5 g of 5β-(3'-oxo-4'-(4''-fluoro)-phenoxy-but-1'-trans-1'-enyl)-2α,4α-dihydroxy-cyclopentane-1α-acetic acid-γ-lactone-4-p-phenylbenzoate in dry THF (50 ml) was added pyrrolidone-hydrotribromide (3 g) and the mixture was stirred for 3 hours at room temperature. After dilution with ethyl ether (2 vol. the precipitate was filtered and washed with ethyl ether. The filtrates were collected, washed with aqueous 40% (NH$_4$)$_2$SO$_4$ solution until neutral, dried and evaporated to dryness in vacuum. The crude 1' {, 2' } -dibromo derivative (14 g) so obtained was dissolved in dry benzene (25 ml) and treated with 1.6 ml of pyridine for 12 hours at room temperature.

The benzenic layer was washed with aqueous 4N H$_2$SO$_4$, aqueous 10% NaHCO$_3$ and water until neutral and evaporated to dryness. After filtration on silica gel (50 g) using as eluent methylene chloride-cyclohexane(80:20), one obtained 3.8 g of pure 5β-[2'-bromo-3'-oxo-4'-(4''-fluoro)-phenoxy-but-1'-trans-1'-enyl]-2α,4α-dihydroxy-cyclopentane-1α-acetic acid-γ-lactone-4-p-phenylbenzoate.

EXAMPLE 8

A solution of dimethyl-[2-oxo-4-(4'-fluoro)-phenoxy]-butyl-phosphonate (0.79 g) in dry benzene (5 ml) was added dropwise to a suspension of NaH (80% dispersion in mineral oil, 72 mg) in dry benzene (8 ml) and the mixture was stirred for one hour. After addition of N-chloro-succinimide (0.33 g) and further stirring for 30 minutes, the benzene solution was filtered and the so obtained dimethyl-[1-chloro-2-oxo-4-(4'-fluoro)-phenoxy]-butyl-phosphonate was added to a suspension of NaH (80% dispersion in mineral oil, 72 mg) in dry benzene. After 20 minutes, 5β-formyl-2α,4α-dihydroxy-cyclopentane-1α-acetic acid-γ-lactone-4-p-phenylbenzoate (0.7 g) in benzene (25 ml) was added to the carbanion solution and the reaction mixture was stirred for 20 minutes at room temperature. After addition of aqueous 50% NaH$_2$PO$_4$ solution, the organic layer was separated, washed with water until neutral, evaporated to a small volume and the residue was absorbed on silica gel (30 g). Elution with methylene chloride afforded 0.72 g of 5β-[2'-chloro-3'-oxo-5'-(4"-fluoro)-phenoxy-pent-1'-trans-1'-enyl]-2α,4α-dihydroxy-cyclopentane-1α-acetic acid-γ-lactone-4-p-phenylbenzoate.

EXAMPLE 9

Using in the procedure of Example 8, N-chloroacetamide instead of N-Cl-succinimide and dimethyl-[2-oxo-3-(4"-fluoro)-phenyl]-propyl-phosphonate to form the carbanion, 0.71 g of 5β-[2'-chloro-3-oxo-4'-(4"-fluoro)-phenoxy-but-1'-trans-1'-enyl]-2α,4α-dihydroxy-cyclopentane-1α-acetic acid-γ-lactone-4-p-phenylbenzoate were prepared.

EXAMPLE 10

A solution of 5β-(2'-bromo-3'-oxo-5'-phenyl-pent-1'-trans-1'-enyl)-2α,4α-dihydroxy-cyclopentane-1α-acetic acid-γ-lactone-4-p-phenylbenzoate (51.5 g) in dimethoxyethane (150 ml) was added to a 0.07 M zinc borohydride solution in ethyl ether (3 l) and the mixture was stirred for 3 hours. After destroying the excess reagent with aqueous 2N sulfuric acid, the organic layer was separated, washed with water until neutral and dried. The usual work-up afforded a crude mixture of the two 3'S and 3'R hydroxy epimers. Separation on silica gel column (benzene: ethyl ether 80:20) yielded 27 g of 5β-(2'-bromo-3'S-hydroxy-5'-phenyl-pent-1'-trans-1'-enyl)-2α,4α-dihydroxy-cyclopentane-1α-acetic acid-γ-lactone-4-p-phenylbenzoate, m.p. 102–104° C.[α]$_D$= −68.8° [α]$_{365}$= −327.3 (C=0.5% CHCl$_3$) and 15 g of the 15'R-isomer m.p. 148–149° C.[α]$_D$= −82.2° [α]$_{365}$= −403° (C=0.5%, CHCl$_3$).

EXAMPLE 11

Borontrifluoride ethereate(0.02 ml) was added to a solution of 5β-(2'-bromo-3'S-hydroxy-5'-phenyl-pent-1'-trans-1'-enyl)-2α,4α-dihydroxy-cyclopentane-1α-acetic acid-γ-lactone-4-p-phenylbenzoate (1.08 g) in methylene chloride, cooled at −10° C. and then the mixture was treated with an excess of a diazomethane solution in methylene chloride until a persistent yellow color.

The organic phase was heated to room temperature washed with aqueous 5% NaHCO$_3$ and with water until neutral, dried and evaporated to dryness. Crystallization from methanol afforded 1 g of 3'S-methoxy derivative, m.p. 126°–127° C.[α]$_D$= −77.5[α]$_{365}$= −341° (C=0.5%, CHCl$_3$). Similarly, a solution, in methylene chloride, of the crude mixture of 3'S and 3'R-alcohols (1.1 g), was treated with BF$_3$ etherate and diazomethane, as above described. The resulting mixture of 3'S and 3'R-methoxy compounds (1.12 g) was chromatographed on silica gel (40 g) using benzene-ethyl ether 90:10 as eluent, so obtaining the 3'-S-methoxy derivative (0.6 g) and 5β-(2'-bromo-3'R-methoxy-5'-phenyl-pent-1'-trans-1'-enyl)-2α,4α-dihydroxy-cyclopentane-1α-acetic acid-γ-lactone-4-p-phenylbenzoate (0.32 g), m.p. 115°–117° C.[α]$_D$= −68.3° [α]$_{364}$= −348.4° (C=0.5%, CHCl$_3$).

EXAMPLE 12

A stirred solution of 5β-[2'-chloro-3'-oxo-4'(4"-fluoro)-phenoxy-but-1'-trans-1'-enyl]-2α,4α-dihydroxy-cyclopentane-1α-acetic acid-γ-lactone-4-p-phenylbenzoate (0.7 g) in methanol was cooled at −5° ÷ −8° C. and treated with NaBH$_4$ (58 mg). After 30 minutes the reaction of trans-enone was complete and the mixture was treated with anhydrous K$_2$CO$_3$ (0.21 g) and stirred for additional two hours. The excess reagent was destroyed by cautious addition of 15% aqueous acetic acid until pH 6.5 and then the methanol was evaporated in vacuum. The residue was partitioned between water and ethylacetate and the organic layer, after the usual work-up, was concentrated to a small volume and absorbed on silica gel.

Elution with methylene chloride-ethyl ether 60:40 afforded 0.27 g of 5β-[2'-chloro-3'S-hydroxy-4'-(4"-fluoro)-phenoxy-but-1'-trans-1'-enyl]-2α,4α-dihydroxy-cyclopentane-1α-acetic acid-γ-lactone and 0.145 g of 3'R-hydroxy-epimer. A solution of the 3'S-alcohol in benzene was treated with 1,4-diox-2-ene and p-toluensulphonic acid (0.005 g) for 4 hours at room temperature. Pyridine (0.15 ml) was added and the solvents were evaporated in vacuum obtaining 0.42 g of the corresponding 3',4-bis-DIOX-ether.

EXAMPLE 13

The α-halo-α,β-unsaturated ketones, which had been prepared according to the procedure of the Examples 1–9, were reduced using zincborohydride, as in the procedure of Example 10, or sodium borohydride, as in the procedure of Example 12, affording a 4-ester, preferably a 4-p-phenylbenzoate, of the following 2α,4α-dihydroxy-cyclopentane-1α-acetic acid-γ-lactone derivatives:

5β-[2'-bromo-3'S-hydroxy-5'-(4"-fluoro)-phenyl-pent-1'-trans-1'-enyl]-;

5β-[2'-bromo-3'S-hydroxy-5'-(3"-chloro)-phenyl-pent-1'-trans-1'-enyl]-;

5β-[2'-bromo-3'S-hydroxy-5'-(3"-trifluoromethyl)-phenyl-pent-1'-trans-1'-enyl]-;

5β-[2'-bromo-3'S-hydroxy-5'-(4"-methoxy)-phenyl-pent-1'-trans-1'-enyl]-;

5β-(2'-bromo-3'S-hydroxy-4'-phenyl-but-1'-trans-1'-enyl)-;

5β-(2'-bromo-3'S-hydroxy-6'-phenyl-hex-1'-trans-1'-enyl)-;

5β-(2'-bromo-3'S-hydroxy-4'S-methyl-5'-phenyl-pent-1'-trans-1'-enyl)-;

5α-(2'-bromo-3'S-hydroxy-4'S-methyl-4'-phenoxy-but-1!-trans-1'-enyl)-;

5β-(2'-bromo-3'S-hydroxy-4'R-methyl-4'-phenoxy-but-1'-trans-1'-enyl)-;

5β-(2'-bromo-3'S-hydroxy-4'-phenoxy-but-1'trans-1'-enyl)-;

5β-(2'-bromo-3'S-hydroxy-4'-benzyloxy-but-1'-trans-1'-enyl)-;

5β-(2'-bromo-3'S-hydroxy-4'-(4"-methoxy)-phenoxy-but-1'-trans-1'-enyl]-;

5β-[2'-bromo-3'S-hydroxy-4'-(4"-fluoro)-phenoxy-but-1'-trans-1'-enyl]-;

[α]$_D$= −70° [α]$_{365}$= −315° (C=0.5%, CHCl$_3$);

5β-[2'-bromo-3'S-4'-(3"-chloro)-phenoxy-but-1'-trans-1'enyl]-;

5β-[2'-bromo-3'S-4'-(3"-trifluoromethyl)-phenoxy-but-1'-trans-1'-enyl]-;

[α]$_D$= −62° [α]$_{365}$= −285° (C=0.5%, CHCl$_3$);

5β-[2'-chloro-3'S-hydroxy-5'-(4"-fluoro)-phenoxy-pent-1'-trans-1'-enyl]-;

5β-[2'-chloro-3'S-hydroxy-4'-(4"-fluoro)-phenoxy-but-1'-trans-1'-enyl]-;

5β-[2'-bromo-3'R-hydroxy-5'-(4''-fluoro)-phenyl-pent-1'-trans-1'-enyl]-;

5β-[2'-bromo-3'R-hydroxy-5'-(3''-chloro)-phenyl-pent-1'-trans-1'-enyl]-;

5β-[2'-bromo-3'R-hydroxy-5'-(3''-trifluoromethyl)-phenyl-pent-1'-trans-1'-enyl]-;

5β-[2'-bromo-3'R-hydroxy-5'-(4''-methoxy)-phenyl-pent-1'-trans-1'-enyl];

5β-(2'-bromo-3'R-hydroxy-4'-phenyl-but-1'-enyl)-;

5β-(2'-bromo-3'-R-hydroxy-6'-phenyl-hex-1'-trans-1'-enyl)-;

5β-(2'-bromo-3'R-hydroxy-4'S-methyl-5'-phenyl-pent-1'-trans-1'-enyl)-;

5β-(2'-bromo-3'R-hydroxy-4'S-methyl-4'-phenoxy-but-1'-trans-1'-enyl)-;

5β-(2'-bromo-3'R-hydroxy-4'R-methyl-4'-phenoxy-but-1'-trans-1'-enyl)-;

5β-(2'-bromo-3'R-hydroxy-4'-phenoxy-but-1'-trans-1'-enyl)-;

5β-(2'-bromo-3'R-hydroxy-4'-benzyloxy-but-1'-trans-1'-enyl)-;

5β-[2'-bromo-3'R-hydroxy-4'-(4''-methoxy)-phenoxy-1'-trans-1'-enyl]-;

5β-[2'-bromo-3'R-hydroxy-4'-(4''-fluoro)-phenoxy-but-1'-trans-1'-enyl]-;

[α9 $_D$ = −72° [α]$_{365}$ = −315° (C=0.5%, CHCl$_3$);

5β-[2'-bromo-3'R-hydroxy-4'-(3''-chloro)-phenoxy-but-1'-trans-1'-enyl]-;

5β-[2'-bromo-3'R-hydroxy-4''-(3''-trifluoromethyl)-phenoxy-but-1'-trans-1'-enyl]-;

[α]$_D$ = −62° [α]$_{365}$ = −285° (C=0.5%, CHCl$_3$);

5β-[2'-chloro-3'R-hydroxy-5'-(4''-fluoro)-phenoxy-pent-1'-trans-1'-enyl]-;

5β-[2'-chloro-3'R-hydroxy-4'-(4''-fluoro)-phenoxy-but-1'-trans-1'-enyl]-;

as a mixture of the two epimeric alcohols, which was chromatographically separated on silica gel or used as such in the following Examples.

EXAMPLE 14

Using diazoethane in the procedure of Example 11, 5β-(2'-bromo-3'S-ethoxy-5'-phenyl-pent-1'-trans-1'-enyl)-2α,4α-dihydroxy-cyclopentane-1α-acetic acid-γ-lactone-4-p-phenylbenzoate was obtained.

EXAMPLE 15

A solution of 5β-(2'-bromo-3'S-hydroxy-4'-phenoxy-but-1'-trans-1'-enyl)-2α,4α-dihydroxy-cyclopentane-1α-acetic acid-γ-lactone-4-p-phenylbenzoate, [α]$_D$ −71° (C=0.5%, CHCl$_3$) (0.13 g) in dry dimethylformamide (5 ml) was stirred in the presence of barium oxide (0.12 g) and benzyl bromide (0.1 g) for five days. After filtration, the excess solvent was evaporated in vacuum and the residue was partitioned between ethyl ether and water. The organic phase, after the usual work-up, was concentrated and absorbed on silica gel. Elution with benzene/ethyl ether (85:15) afforded 0.098 g of 5β-(2'-bromo-3'S-benzyloxy-4'-phenoxy-but-1'-trans-1'-enyl)-2α,4α-dihydroxy-cyclopentane-1α-acetic acid-γ-lactone-4-p-phenylbenzoate.

EXAMPLE 16

A solution of 5β-(2'-bromo-3'S-hydroxy-5'-phenyl-pent-1'-trans-1'-enyl)-2α,4α-dihydroxy-cyclopentane-1α-acetic acid-γ-lactone-4-p-phenylbenzoate (2.72 g) in dry methanol (30 ml) was stirred with 0.42 of anhydrous K$_2$CO$_3$ at room temperature for 2–5 hours.

The mixture was then treated with aqueous NH$_2$SO$_4$, until pH 5, the methanol was evaporated in vacuum and the residue was partitioned between ethyl ether and a phosphate buffer (pH 6.8). After evaporation of the solvent the residue was absorbed on silica gel (30 g) and eluted with ethyl ether to remove methyl-p-phenylbenzoate and with ethyl acetate to obtain 5β-(2'-bromo-3'S-hydroxy-5'-phenyl-pent-1'-trans-1'-enyl)-2α,4α-dihydroxy-cyclopentane-1α-acetic acid-γ-lactone, [α]$_D$ = −12.7° [α]$_{365}$ = −47.5 (C=0.5% CHCl$_3$).

EXAMPLE 17

According to Example 16, selective saponification of the ester function of the compounds prepared in the Examples 10–15, allowed to obtain the following 2α,4α-dihydroxy-cyclopentane-1α-acetic acid-γ-lactone derivatives:

5β-[2'-bromo-3'S-hydroxy-5'-(4''-fluoro)-phenyl-pent-1'-trans-1'-enyl]-;

5β-[2'-bromo-3'S-hydroxy-5'-(3''-chloro)-phenyl-pent-1'-trans-1'-enyl];

5β-[2'-bromo-3'S-hydroxy-5'-(3''-trifluoromethyl)-phenyl-pent-1'-trans-1'-enyl]-

5β-[2'-bromo-3'S-hydroxy-5'-(4'')methoxy)-phenyl-pent-1'-trans-1'-enyl]-;

5β-(2'-bromo-3'S-hydroxy-4'-phenyl-but-1'-trans-1'-enyl)-;

5β-(2'-bromo3'S-hydroxy-6'-phenyl-hex-1'-trans-1'-enyl]-;

5β-(2'-bromo-3'S-hydroxy-4'S-methyl-5'-phenyl-pent-1'-trans-1'-enyl)-;

5β-(2'-bromo-3'S-hydroxy-4'S-methyl-4'-phenoxy-but-1'-trans-1'-enyl)-;

5β-(2'-bromo-3'S-hydroxy-4'R-methyl-4'-phenoxy-but-1'-trans-1'-enyl)-;

5β-(2'-bromo-3'S-hydroxy-4'-phenoxy-but-1'-trans-1'-enyl)-;

5β-(2'-bromo-3'S-hydroxy-4'-benzyloxy-but-1'-trans-1'-enyl)-;

5β-[2'-bromo-3'S-hydroxy-4'-(4''-methoxy)-phenoxy-but-1'-trans-1'-enyl]-;

5β-[2'-bromo-3'S-hydroxy-4'-(4''-fluoro)-phenoxy-but-1'-trans-1'-enyl]-;

5β-[2'-bromo-3'S-hydroxy-4'-(3''-chloro)-phenoxy-but-1'-trans-1'-enyl]-;

5β-[2'-bromo-3'S-hydroxy-4'-(3''-trifluoromethyl)-phenoxy-but-1'-trans-1'-enyl]-;

5β-[2'-chloro-3'S-hydroxy-5'-(4''-fluoro)-phenoxy-pent-1'-trans-1'-enyl]-;

5β-[2'-chloro-3'S-hydroxy-4'-(4''-fluoro)-phenoxy-but-1'-trans-1'-enyl]-;

5β-(2'-bromo-3'-S-hydroxy-5'-phenyl-pent-1'-trans-1'enyl)-;

5β-(2'-bromo-3'S-methyoxy-5'-phenyl-pent-1'-trans-1'enyl)-;

5β-(2'-bromo-3'S-ethoxy-5'-phenyl-pent-1'trans-1-enyl)-;

5β-(2'-bromo-3'S-methoxy-4'S-methyl-5'-phenyl-pent-1'-trans-1'-enyl)-;

5β-(2'-bromo-3'S-methoxy-4'R-methyl-5'-phenyl-pent-1'-trans-1'-enyl)-;

5β-(2'-bromo-3'S-benzyloxy-4'-phenoxy-but-1'-trans-1'-enyl)-;

as well as their 3'R-epimeric-derivatives.

EXAMPLE 18

A solution of 0.25 g of 5β-[2'-bromo-3'S-hydroxy-4'-(3''-trifluoromethyl)-phenoxy-but-1'-trans-1'-enyl]-2α,-

4α-dihydroxy-cyclopentane-1α-acetic acid-γlactone, $[α]_D= -13.2°$ (C=0.5% CHCl$_3$) in methylene chloride (8 ml) was treated with 2.3-dihydropyran (0.12 ml) and p-toluenesulfonic acid (7 mg). After 2 hours the mixture was washed with 10% aqueous NaHCO$_3$ and water until neutral. The organic solution was dried on Na$_2$SO$_4$ and the solvents were evaporated to obtain 5β[2'-bromo-3'-S-hydroxy-4'-(3''-trifluoromethyl)-phenoxy-but-1'-trans-1'-enyl]-2α,4α-dihydroxy-cyclopentane-1α-acetic acid-γ-lactone-4,3'-bis-THP-ether (0.33 g ), $[α]_D= -29.5°$ (C=1% CHCl$_3$).

Using this procedure, the 3',4-bis acetalic ethers (dioxanylethers, α-ethoxy-ethylethers and preferably 2''-tetrahydropyranylethers) of the following 2α,4α-dihydroxy-cyclopentane-1α-acetic acid-γ-lactone derivatives were obtained:

5β-[2'-bromo-3'S-hydroxy-5'-(4''-fluoro)-phenyl-pent-1'-trans-1'-enyl]-;

5β-[2'-bromo-3'S-hydroxy-5'-(3''-chloro)-phenyl-pent-1'-trans-1'-enyl]-;

5β-[2'-bromo-3'S-hydroxy-5'-(3''-trifluoromethyl)-phenyl-pent-1'-trans-1'-enyl]-;

5β-[2'-bromo-3'S-hydroxy-5'-(4''-methoxy)-phenyl-pent-1'-trans-1'-enyl]-;

5β-(2'-bromo-3'S-hydroxy-4'-phenyl-but-1'-trans-1'-enyl)-;

5β-(2'-bromo-3'S-hydroxy-6'-phenyl-hex-1'-trans-1'-enyl)-;

5β-(2'-bromo-3'S-hydroxy-4'S-methyl-5'-phenyl-pent-1'-trans-1'-enyl)-;

5β-(2'-bromo-3'S-hydroxy-4'S-methyl-4'-phenoxy-but-1'-trans-1'-enyl)-;

5β-(2'-bromo-3'S-hydroxy-4'R-methyl-4'-phenoxy-but-1'-trans-1'-enyl)-;

5β-(2'-bromo-3'S-hydroxy-4'-phenoxy-but-1'-trans-1'-enyl)-;

5β-(2'-bromo-3'S-hydroxy-4'-benzyloxy-but-1'-trans-1'-enyl);

5β-[2'-bromo-3'S-hydroxy-4'-(4''-methoxy)-phenoxy-but-1'-trans-1'-enyl]-;

5β-[2'-bromo-3'S-hydroxy-4'-(4''-fluoro)-phenoxy-but-1'-trans-1'-enyl]-;

5β-[2'-bromo-3'S-hydroxy-4'-(3''-chloro)-phenoxy-but-1'-trans-1'-enyl]-;

5β-[2'-bromo-3'S-hydroxy-4'-(3''-trifluoromethyl)-phenoxy-but-1'-trans-1'-enyl]-;

5β-[2'-chloro-3'S-hydroxy-5'-(4''-fluoro)-phenoxy-pent-1'-trans-1'-enyl]-;

5β-[2'-chloro-3'S-hydroxy-4'-(4''-fluoro)-phenoxy-but-1'-trans-1'-enyl]-;

5β-(2'-bromo-3'S-hydroxy-5'-phenyl-pent-1'-trans-1'-enyl)-;

as well as their 3'R-epimeric-derivatives.

EXAMPLE 19

A solution of 5β-(2'-bromo-3'S-methoxy-5-phenyl-pent-1'-trans-1'-enyl)-2α,4α-dihydroxy-cyclopentane-1α-acetic acid-γ-lactone (4.4 g) in methylene chloride (50 ml) was treated with 2,3-dihydropyran (1.3 ml) and p-toluensulfonic acid (20 mg). After 2 hours the methylene chloride solution was washed with 10% aqueous NaHCO$_3$, with water and dried. The solvent was evaporated so obtaining 5.34 g of the corresponding 4-THP-ether, $[α]_D= -3.9°$ (C=1% CHCl$_3$). Analogously, starting from the 3 ⅔-alkoxy derivatives of the Example 17, by treatment with a vinyl ether (f.e. 2,3-dihydropyran, 1,4-diox-2-ene and α-ethoxy-vinyl ether), the 4-acetalic ethers (2''-1'',4''-dioxanylethers, α-ethoxy-ethylethers and preferably 2''-tetrahydropyranylethers) of the following 2α,4α-dihydroxy-cyclopentane-1α-acetic acid-γ-lactone derivatives were obtained:

5β-(2'-bromo-3'S-methoxy-5'-phenyl-pent-1'-trans-1'-enyl)-;

5β-(2'-bromo-3'S-methoxy-5'-phenyl-pent-1'-trans-1'-enyl)-;

5β-(2'-bromo-3'S-ethoxy-5'-phenyl-pent-1'-trans-1'-enyl)-;

5β-(2'-bromo-3'S-methoxy-4'S-methyl-5'-phenyl-pent-1'-trans-1'-enyl)-;

5β-(2'-bromo-3'-S-methoxy-4'R-methyl-5'-phenyl-pent-1'-trans-1'-enyl)-;

5β-(2'-bromo-3'S-benzyloxy-4'-phenoxy-but-1'-trans-1'-enyl)-;

as well as their 3'R-epimeric compounds.

EXAMPLE 20

A 0.5 M solution of DIBA in toluene (9.8 ml) was added over a 15 minutes period to a stirred solution of 5β-[2'-bromo-3'S-hydroxy-4'-(3''-trifluoromethyl)-phenoxy-but-1'-trans-1'-enyl]-2α,4α-dihydroxy-cyclopentane-1α-acetic acid-γ-lactone-3',4-bis-THP-ether (1.14 g) in toluene (20 ml) and cooled to $-70°$ C.

After 30 minutes, the mixture was treated with 5 ml of 2M 2-propanol solution in toluene, heated to room temperature and then aqueous saturated NaH$_2$PO$_4$ solution (5 ml) was added. The mixture was stirred for 4 hours and, after addition of anhydrous Na$_2$SO$_4$, filtered.

The solvent was evaporated to dryness affording 1.1 g of 5β-[2'-bromo-3'S-hydroxy-4'-(3''-trifluoromethyl)-phenoxy-but-1'-trans-1'-enyl]-2α,4α-dihydroxy-cyclopentane-1α-ethanal-γ-lactol-3',4-bis-THP-ether.

EXAMPLE 21

5β-(2'-bromo-3'S-methoxy-5'-phenyl-pent-1'-trans-1'-enyl)-2α,4α-dihydroxy-cyclopentane-1α-ethanal-γ-lactol-4-THP-ether 0.65 g $[α]_D= -4°,[α]_{365}= -27.3°$ (C=1% CHCl$_3$) was obtained starting from a solution of the corresponding γ-lactone (0.8 g) in toluene (10 ml) by reduction with 0.5 M DIBA in benzene (4.4 ml) working at $-70°$ C.

EXAMPLE 22

Under a nitrogen atmosphere, a mixture of a 70% solution of sodium bis-(2-methoxy-ethoxy)-aluminium hydride in benzene (0.58 ml) and toluene (5 ml) was added to a stirred solution of 5β-[2'-chloro-3'S-hydroxy-4'-(4''-fluoro)-phenoxy-but-1'-trans-1'enyl]-2α,4α-dihydroxy-cyclopentane-1α-acetic acid-γ-lactone-4,3'-bis-DIOX-ether, cooled at $-60°$ C. The stirring was continued for 3 hours and the excess reagent was destroyed by addition of acetone-toluene (1:1) 10 ml. The mixture was warmed at room temperature, treated with 2 ml of aqueous saturated NaH$_2$PO$_4$ solution and stirred for 4 hours. The precipitate was filtered out and the organic solvents were evaporated to dryness affording 0.41 g of 5β-[2'-chloro-3'S-hydroxy-4'-(4''-fluoro)-phenoxy-but-1'-trans-1'-enyl]-2α,4α-dihydroxy-cyclopentane-1α-ethanal-γ-lactol-3',4-bis-DIOX-ether.

EXAMPLE 23

By reduction of a γ-lactone of the Examples 18 and 19, using as reducing agents DIBA, according to the procedure of Examples 20 and 21, or sodium bis-(2-methoxy-ethoxy)-aluminium hydride, according to the procedure of Example 22, the following 2α,4α-dihydroxy-cyclopentane-1α-ethanal-γ-lactol derivatives:

5β-[2'-bromo-3'S-hydroxy-5'-(4"-fluoro)-phenyl-pent-1'-trans-1'-enyl]-;

5β-[2'-bromo-3'S-hydroxy-5'-(3"-chloro)-phenyl-pent-1'-trans-1'-enyl]-;

5β-[2'-bromo-3'S-hydroxy-5'-(3"-trifluoromethyl)-phenyl-pent-1'-trans-1'-enyl]-;

5β-2'-bromo-3'S-hydroxy-5'-(4"-methoxy)-phenyl-pent-1'-trans-1'-enyl]-;

5β-(2'-bromo-3'S-hydroxy-4'-phenyl-but-1'-trans-1'-enyl)-;

5β-(2'-bromo-3'S-hydroxy-6'-phenyl-hex-1'-trans-1'-enyl)-;

5β-(2'-bromo-3'S-hydroxy-4'S-methyl-5'-phenyl-pent-1'trans-1'-enyl)-;

5β-(2'-bromo-3'S-hydroxy-4'S-methyl-4'-phenoxy-but-1'-trans-1'-enyl)-;

5β-(2'-bromo-3'S-hydroxy-4'R-methyl-4'-phenoxy-but-1'-trans-1'-enyl)-;

5β-(2'-bromo-3'S-hydroxy-4'-phenoxy-but-1'-trans-1'-enyl)-;

5β-(2'-bromo-3'S-hydroxy-4'-benzyloxy-but-1'-trans-1'-enyl-)-;

5β-[2'-bromo-3'S-hydroxy-4'-(4"-methoxy)-phenoxy-but-1'-trans-1'-enyl]-;

5β-[2'-bromo-3'S-hydroxy-4'-(4"-fluoro)-phenoxy-but-1'-trans-1'-enyl]-;

5β-[2'-bromo-3'S-hydroxy-4'-(3"-chloro)-phenoxy-but-1'-trans-1'-enyl]-;

5β-[2'-bromo-3'S-hydroxy-4'-(3"-trifluoromethyl)-phenoxy-but-1'-trans-1'-enyl]-;

5β-[2'-chloro-3'S-hydroxy-5'-(4"-fluoro)-phenoxy-pent-1'-trans-1'-enyl]-;

5β-[2'-chloro-3'S-hydroxy-4'-(4"-fluoro)-phenoxy-but-1'-trans-1'-enyl]-;

5β-(2'-bromo-3'S-hydroxy-5'-phenyl-pent-1'-trans-1'-enyl)-, were obtained as 3',4-bis-acetalic ethers (bis-DIOX-ethers; bis-α-ethoxyethyl ethers and preferably bis-THP-ethers) and the following 2α,4α-dihydroxy-cyclopentane-1α-ethanal-γ-lactol derivatives:

5β-(2'-bromo-3'-S-methoxy-5'-phenyl-pent-1'-trans-1'-enyl)-;

5β-(2'-bromo-3'S-methoxy-5'-phenyl-pent-1'-trans-1'-enyl)-;

5β-(2'-bromo-3'S-ethoxy-5'-phenyl-pent-1'-trans-1'-enyl)-;

5β-(2'-bromo-3'S-methoxy-4'S-methyl-5'-phenyl-pent-1'-trans-1'-enyl)-;

5β-(2'-bromo-3'S-methoxy-4'R-methyl-5'-phenyl-pent-1'-trans-1'-enyl)-;

5β-(2'-bromo-3'S-benzyloxy-4'-phenoxy-but-1'-trans-1'-enyl)-, were obtained as 4-acetalic ethers (DIOX-ethers, α-ethoxy-ethylethers and preferably THP-ethers).

EXAMPLE 24

5c-9α,11α-dihydroxy-15S-methoxy-20,19,18-trinor-prost-5-en-13-ynoic acid-11-THP-ether (1.1 g), $[\alpha]_D = +11.6°[\alpha]_{365} = +13.2°$ (C=1% CHCl$_3$) was obtained by addition of a solution of 1.28 g of 5β-(2'-bromo-3'S-methoxy-5'-phenyl-pent-1'-trans-1'-enyl)-2α,4α-dihydroxy-cyclopentane-1α-ethanal-γ-lactol-4-THP-ether in benzene (0.6 ml) and DMSO (1.5 ml) to a stirred solution of ylide prepared from triphenyl-(4-carboxybutyl)-phosphonium bromide (5.6 g) and potassium tert-butoxide (3 g) in 12 ml of dry DMSO cooled at 20° C.

The mixture was stirred for 3 hours, diluted with water and extracted with ethyl ether to remove the triphenylphosphine oxide. The ethereal extracts were combined, back-washed with 0.5 N KOH and then discarded.

The alkaline washes were combined with the original alkaline phase, acidified to pH 4.9 and extracted several times with ethyl ether: pentane 1:1. These combined organic extracts were washed with saturated (NH$_4$)$_2$SO$_4$ and evaporated to dryness affording the prostynoic derivative.

EXAMPLE 25

Under a nitrogen atmosphere, cooling the reaction mixture at 15°-20° C., a solution of potassium tert-butoxide (5.03 g) in dry DMSO was added to a solution of 10.25 g of triphenyl-(4-carboxybutyl)-phosphonium bromide to obtain a deep red-yellow solution of the ylide in DMSO. To this stirred solution (cooled to 15–17°), a solution of 2.06 g of 5β-(2'-bromo-3'S-hydroxy-5'-phenyl-pent-1'-trans-1'-enyl)-2α,4α-dihydroxy-cyclopentane-1α-ethanal-γ-lactol-3',4-bis-THP-ether in DMSO (10 ml) was added. After 4 hours, the mixture was diluted with 0.5 N KOH (60 ml) and extracted with ethyl ether. These ethereal extracts were washed with (2×5) 0.5 N KOH and water until neutral and then discarded.

The aqueous alkaline phases were collected, acidified to pH 4.9 with 2N H$_2$SO$_4$ and extracted with ethyl ether-pentane(1:1)obtaining, after usual work-up, 1.92 g of 5c-9α,11α,15S-trihydroxy-20,19,18-trinor-17-phenyl-prost-5-en-13-ynoic acid-11,15-bis-THP-ether,- $[\alpha]_D = +11.2$ (CHCl$_3$). The methyl ester was obtained by adding an ethereal solution of diazomethane to a solution of the acid until a persistent yellow colour. The solvent was evaporated in vacuum so obtaining 0.8 g of methyl 5c-9α,11α,15S-trihydroxy-20,19,18-trinor-17-phenyl-prost-5-en-13-ynoate-11,15-bis-THP-ether.

EXAMPLE 26

Under a nitrogen atmosphere, NaH (80% in mineral oil, 1.49 g) suspension in dry DMSO (40 ml) was heated at 60°-65° C. for 3 hours until no more hydrogen evolved; then the solution was cooled to 15°-17° and treated with a solution of triphenyl-(4-carboxybutyl)-phosphoniumbromide (10.9 g) in DMSO, under vigorous stirring.

To the resulting deep red-orange solution, a solution of 5β-[2'-chloro-3'S-hydroxy-4'-(4"-fluoro)-phenoxy-but-1'-trans-1'-enyl]-2α,4α-dihydroxy-cyclopentane-1α-ethanal-γ-lactol-3',4'-bis-DIOX-ether (1.71 g) in DMSO (10 ml) was added, cooling the reaction mixture to 15°-20° C. After hours it was diluted with water (50 ml) and the aqueous medium was extracted repeatedly with ethyl ether to remove triphenylphosphine.

These organic extracts were back-washed with 1 N NaOH, with water and then discarded.

The combined aqueous phases were acidified to pH 4.4 with 2N sulfuric acid and extracted with ethyl ether: pentane (1:1; these organic extracts were combined, washed with aqueous saturated (NH$_4$)$_2$SO$_4$ and then evaporated to dryness to afford 1.52 g of 5c-9α,11α,15S-trihydroxy-20,19,18,17-tetranor-16-(4'-fluoro)-phenoxy-prost-5-en-13-ynoic acid-11,15-bis-DIOX-ether.

EXAMPLE 27

A γ-lactol, which had been prepared in the Examples 20–23, was reacted with the ylide obtained by treatment of the triphenyl-(4-carboxybutyl)-phosphonium bromide with potassium tert-butoxide, according to the procedure of the Examples 24 and 25, or with NaH—DMSO, according to the procedure of the Example 26, and the following 11,15-bis-acetalic ethers (DIOX-ethers,α-ethoxyethyl ethers and preferably THP-ethers) were prepared:

5c-9α,11α,15S-trihydroxy-20,19,18-trinor-17-(4'-fluoro)-phenyl-prost-5-en-13-ynoic acid;

5c-9α,11α,15S-trihydroxy-20,19,18-trinor-17-(3'-chloro)-phenyl-prost-5-en-13-ynoic acid;

5c-9α,11α,15S-trihydroxy-20,19,18-trinor-17-(3'-trifluoromethyl)-phenyl-prost-5-en-13-ynoic acid;

5c-9α,11α,15S-trihydroxy-20,19,18-trinor-17-(4'-methoxy)-phenyl-prost-5-en-13-ynoic acid;

5c-9α,11α,15S-trihydroxy-20,19,18,17-tetranor-16-phenyl-prost-5-en-13-ynoic acid;

5c-9α,11α,15S-trihydroxy-20,19-dinor-18-phenyl-prost-5-en-13-ynoic acid;

5c-9α,11α,15S-trihydroxy-20,19,18-trinor-17-phenyl-prost-5-en-13-ynoic acid;

5c-9α,11α,15S-trihydroxy-20,19,18-trinor-16S-methyl-17-phenyl-prost-5-en-13-ynoic acid;

5c-9α,11α-15S-trihydroxy-20,19,18-trinor-16R-methyl-17-phenyl-prost-5-en-13-ynoic acid;

5c-9α,11α,15S-trihydroxy-20,19,18,17-tetranor-16S-methyl-16-phenoxy-prost-5-en-13-ynoic acid;

5c-9α,11α,15S-trihydroxy-20,19,18,17-tetranor-16R-methyl-16-phenoxy-prost-5-en-13-ynoic acid;

5c-9α,11α,15S-trihydroxy-20,19,18,17-tetranor-16-benzyloxy-prost-5-en-13-ynoic acid;

5c-9α,11α,15S-trihydroxy-20,19,18,17-tetranor-16-phenoxy-prost-5-en-13-ynoic acid;

5c-9α,11α,15S-trihydroxy-20,19,18,17-tetranor-16-(4'-methoxy)-phenoxy-prost-5-en-13-ynoic acid;

5c-9α,11α,15S-trihydroxy-20,19,18,17-tetranor-16-(4'-fluoro)-phenoxy-prost-5-en-13-ynoic acid;

5c-9α,11α,15S-trihydroxy-20,19,18,17-tetranor-16-(3'-chloro)-phenoxy-prost-5-en-13-ynoic acid;

5c-9α,11α,15S-trihydroxy-20,19,18,17-tetranor-16-(3'-trifluoromethyl)-phenoxy-prost-5-en-13-ynoic acid;

5c-9α,11α,15S-trihydroxy-20,19,18-trinor-17-(4'-fluoro)-phenoxy-prost-5-en-13-ynoic acid;

5c-9α,11α,15R-trihydroxy-20,19,18-trinor-17-(4'-fluoro)-phenyl-prost-5-en-13-ynoic acid;

5c-9α,11α,15R-trihydroxy-20,19,18-trinor-17-(3'-chloro)-phenyl-prost-5-en-13-ynoic acid;

5c-9α,11α,15R-trihydroxy-20,19,18-trinor-17-(3'-trifluoromethyl)-phenyl-prost-5-en-13-ynoic acid;

5c-9α,11α,15R-trihydroxy-20,19,18-trinor-17-(4'-methoxy)-phenyl-prost-5-en-13-ynoic acid;

5c-9α,11α,15R-trihydroxy-20,19,18,17-tetranor-16-phenyl-prost-5-en-13-ynoic acid;

5c-9α,11α,15R-trihydroxy-20,19-dinor-18-phenyl-prost-5-en-13-ynoic acid;

5c-9α,11α,15R-trihydroxy-20,19,18-trinor-17-phenyl-prost-5-en-13-ynoic acid;

5c-9α,11α,15R-trihydroxy-20,19,18-trinor-16S-methyl-17-phenyl-prost-5-en-13-ynoic acid;

5c-9α,11α-15R-trihydroxy-20,19,18-trinor-16R-methyl-17-phenyl-prost-5-en-13-ynoic acid;

5c-9α,11α,15R-trihydroxy-20,19,18,17-tetranor-16S-methyl-16-phenoxy-prost-5-en-13-ynoic acid;

5c-9α,11α,15R-trihydroxy-20,19,18,17-tetranor-16R-methyl-16-phenoxy-prost-5-en-13-ynoic acid;

5c-9α,11α,15R-trihydroxy-20,19,18,17-tetranor-16-benzyloxy-prost-5-en-13-ynoic acid;

5c-9α,11α,15R-trihydroxy-20,19,18,17-tetranor-16-phenoxy-prost-5-en-13-ynoic acid;

5c-9α,11α,15R-trihydroxy-20,19,18,17-tetranor-16-(4'-methoxy)-phenoxy-prost-5-en-13-ynoic acid;

5c-9α,11α,15R-trihydroxy-20,19,18,17-tetranor-16-(4'-fluoro)-phenoxy-prost-5-en-13-ynoic acid;

5c-9α,11α,15R-trihydroxy-20,19,18,17-tetranor-16-(3'-chloro)-phenoxy-prost-5-en-13-ynoic acid;

5c-9α,11α,15R-trihydroxy-20,19,18,17-tetranor-16-(3'-trifluoromethyl)-phenoxy-prost-5-en-13-ynoic acid;

5c-9α,11α,15R-trihydroxy-20,19,18-trinor-17-(4'-fluoro)-phenoxy-prost-5-en-13-ynoic acid;

as well as the following 11-acetalic ethers (DIOX-ethers, α-ethoxy-ethyl ethers and preferably THP-ethers):

5c-9α,11α-dihydroxy-15S-methoxy-20,19,18-trinor-17-phenyl-prost-5-en-13-ynoic acid;

5c-9α,11α-dihydroxy-15S-ethoxy-20,19,18-trinor-17-phenyl-prost-5-en-13-ynoic acid;

5c-9α,11α-dihydroxy-15S-methoxy-20,19,18-trinor-16S-methyl-17-phenyl-prost-5-en-13-ynoic acid;

5-9α,11α-dihydroxy-15S-methoxy-10,19,18-trinor-16R-methyl-17-phenyl-prost-5-en-13-ynoic acid;

5c-9α,11α-dihydroxy-15S-benzyloxy-20,19,18,17-tetranor-16-phenoxy-prost-5-en-13-ynoic acid;

5c-9α,11α-dihydroxy-15R-methoxy-20,19,18-trinor-17-phenyl-prost-5-en-13-ynoic acid;

5c-9α,11α-dihydroxy-15R-ethoxy-20,19,18-trinor-17-phenyl-prost-5-en-13-ynoic acid;

5c-9α,11α-dihydroxy-15R-methoxy-20,19,18-trinor-16S-methyl-17-phenyl-prost-5-en-13-ynoic acid;

5c-9α,11α-dihydroxy-15R-methoxy-20,19,18-trinor-16R-methyl-17-phenyl-5-en-13-ynoic acid;

5c-9α,11α-dihydroxy-15R-benzyloxy-20,19,18,17-tetranor-16-phenoxy-prost-5-en-13-ynoic acid.

Afterwards the free acids were converted into their alkyl esters by treatment with a diazoalkane solution.

EXAMPLE 28

To a solution of triphenylphosphine (30 g) in dry acetonitrile, 5-bromo-pentanoic acid-N,N-diethylamide (23.5 g) was added and the mixture was refluxed for 16 hours. After cooling to room temperature, the crystalline product was filtered off to yield 34.2 g of triphenyl-(4-N,N-diethylcarboxamide-butyl)-phosphoniuu bromide. Under a nitrogen atmosphere, a solution of this compound (1.5 g) in DMSO was added to a stirred solution of sodium dimethylsulfoxide carbanion, cooled to 10°–14° C., which had been prepared by heating 115 mg NaH (80%) in 10 ml of DMSO at 60°–65° C. for 3 hours. Then the ylide solution was treated with a solution of 5β-(2'-bromo-3'S-hydroxy-5'-phenyl-pent-1'-trans-1'-enyl)-2α,4α-dihydroxy-cyclopentane-1α-ethanol-γ-lactol-3',4-bis-THP-ether in dry DMSO (4 ml) (0.5 g) for 4 hours at room temperature. The mixture was diluted with water (20 ml) and extracted with ethyl ether-pentane 1:1. The combined ethereal extracts were washed until neutral, concentrated to small volume and the residue was absorbed on silica gel. Elution with benzene ethyl ether (85:15) afforded 0.42 g of 5c-9α,11α,15S-trihydroxy-20,19,18-trinor-17-phenyl-prost-5-en-13-ynoic acid-N,N-diethyl amide-11,15-bis-THP-ether.

A solution of this compound (0.15 g) in dry methanol (10 ml) was treated with p-toluensulfonic acid (8 mg) at room temperature for 2 hours. Pyridine (0.05 ml) was added. The solvent was evaporated in vacuum and the residue was partitioned between water and ethyl ether. The organic extracts were collected, evaporated to dryness and after thin layer chromatography on silica gel, 72 mg of 5c-9α,11α,15S-trihydroxy-20,19,18-trinor-17-phenyl-prost-5-en-13-ynoic acid-N,N-diethylamide were obtained.

EXAMPLE 29

Triphenylphosphine (0.53 g), benzoic acid (0.24 g) and 5c-9α,11α, 15S-trihydroxy-20,19,18-trinor-17-phenyl-prost-5-en-13-ynoic acidmethyl ester-11,15-bis-THP-ether,$[α]_D = +12°$ (CHCl$_3$), (0.45 g) were dissolved in dry benzene (20 ml) and a solution of diethylazo-bis-carboxylate (0.35 g) in benzene (5 ml) was added dropwise to this mixture. After 20 minutes, the organic layer was washed with aqueous 2N H$_2$SO$_4$, water, aqueous 10% NaHCO$_3$ and water until neutral, dried and the solvents evaporated to dryness. The residue was absorbed on silica gel and elution with benzene-ethyl ether afforded 0.41 g of 5c-9β,11α,15S-trihydroxy-20,19,18-trinor-17-phenyl-prost-5-en-13-ynoic acid methyl ester-11,15-bis-THP-ether-9-benzoate.

A sample of this compound (0.14 g) was treated in dry methanol (4.5 ml) with anhydrous potassium carbonate (50 mg) for 3 hours at room temperature. The solvent was evaporated in vacuum and the crude product was partitioned between aqueous 25% NaH$_2$PO$_4$ solution and ethyl acetate. The organic phase was separated and after thin layer chromatography on silica gel, 92 mg of 5c-9β,11α,15S-trihydroxy-20,19,18-trinor-17-phenyl-prost-5-en-13-ynoic acid methyl ester-11,15-bis-THP-ether were obtained. Analogously the following 9-benzoate derivatives:

5c-9β,11α,15S-trihydroxy-20,19,18,17-tetranor-16-(4'-fluoro)-phenoxy-prost-5-en-13-ynoic acid methyl ester-11,15-bis-THP-ether; 5c-9β,11α-dihydroxy-15S-methoxy-20,19,18-trinor-17-phenyl-prost-5-en-13-ynoic acid methyl ester-11-THP-ether, were prepared and after selective hydrolysis the corresponding free 9β-hydroxy compounds were prepared.

EXAMPLE 30

A stirred solution of 5c-9α,11α-dihydroxy-15S-methoxy-20,19,18-trinor-17-phenyl-prost-5-en-13-ynoic acid-methyl ester-11-THP-ether (0.48 g) in acetone (15 ml) was cooled to $-15 \div -12°$ C. and treated with Jones reagent (1.4 ml). After 15 minutes the mixture was diluted with benzene and washed repeatedly with aqueous 30% (NH$_4$)$_2$SO$_4$ solution until neutral. The solvent was evaporated in vacuum to provide 5c-9-oxo-11α-hydroxy-15S-methoxy-20,19,18-trinor-17-phenyl-prost-5-en-13-ynoic acid-methyl ester-11-THP-ether (0.37 g).

EXAMPLE 31

To a stirred solution of 5c-9α,11α,15S-trihydroxy-20,19,18-trinor-17-phenyl-prost-5-en-13-ynoic acid-11,15-bis-THP-ether (0.55 g) in acetone (15 ml), cooled to $-14 \div -10°$ C., Jones reagent (1.4 ml) was added. After 30 minutes, the mixture was diluted with benzene (50 ml) and washed until neautral with saturated (NH$_4$)$_2$SO$_4$ solution. The combined aqueous fractions were extracted with benzene and the organic phases were collected, dried on Na$_2$SO$_4$, evaporated to dryness affording 0.48 g of 5c-9-oxo-11α15S-dihydroxy-20,19,18-trinor-17-phenyl-prost-5-en-13-ynoic acid-11,15-bis-THP-ether.

EXAMPLE 32

Starting from 9-hydroxy-prost-13-ynoic derivatives either as free acids or as their methyl esters, which were prepared in the Examples 24, 25, 26, 27, 28 and 29, oxidation with Jones reagent afforded, either as free acids or their methyl esters, the following 11,15-bis-THP-ethers:

5c-9-oxo-11α,15S-dihydroxy-20,19,18-trinor-17(4'-fluoro)-phenyl-prost-5-en-13-ynoic acid;
5c-9-oxo-11α,15S-dihyroxy-20,19,18-trinor-17-(3'-chloro)-phenyl-prost-5-en-13-ynoic acid;
5c-9-oxo-11α,15S-dihydroxy-20,19,18-trinor-17-(3'-trifluoromethyl)-phenyl-prost-5-en-13-ynoic acid;
5c-9-oxo-11α,15S-dihydroxy-20,19,18-trinor-17-(4'-methoxy)-phenyl-prost-5-en-13-ynoic acid;
5c-9-oxo-11α,15S-dihydroxy-20,19,18,17-tetranor-16-phenyl-prost-5-en-13-ynoic acid;
5c-9-oxo-11α,15S-dihydroxy-20,19-dinor-18-phenyl-prost-5-en-13-ynoic acid;
5c-9-oxo-11α,15S-dihydroxy-20,19,18-trinor-17-phenyl-prost-5-en-13-ynoic acid;
5c-9-oxo-11α,15S-dihydroxy-20,19,18-trinor-16S-methyl-17-phenyl-prost-5-en-13-ynoic acid;
5c-9-oxo-11α,15S-dihydroxy-20,19,18-trinor-16R-methyl-17-phenyl-prost-5-en-13-ynoic acid;
5c-9-oxo-11α,15S-dihydroxy-20,19,18,17-tetranor-16S-methyl-16-phenoxy-prost-5-en-13-ynoic acid;
5c-9-oxo-11α,15S-dihydroxy-20,19,18,17-tetranor-16R-methyl-16-phenoxy-prost-5-en-13-ynoic acid;
5c-9-oxo-11α,15S-dihydroxy-20,19,18,17-tetranor-16-phenoxy-prost-5-en-13ynoic acid; 5c-9-oxo-11α,15S-dihydroxy-20,19,18,17-tetramor-16-benzyloxy-prost-5-en-13-ynoic acid;
5c-9-oxo-11α,15S-dihydroxy-20,19,18,17-tetranor-16-(4'-methoxy)-phenoxy-prost-5-en-13-ynoic acid;
5c-9-oxo-11α,15S-dihydroxy-20,19,18,17-tetranor-16-(4'-fluoro)-phenoxy-prost-5-en-13-ynoic acid;
5c-9-oxo-11α,15S-dihydroxy-20,19,18,17-tetranor-16-(3'-chloro)-phenyoxy-prost-5-en-13-ynoic acid;
5c-9-oxo-11α,15S-dihydroxy-20,19,18,17-tetranor-16-(3'-trifluoromethyl)-phenoxy-prost-5-en-13-ynoic acid;
5c-9oxo-11α,15S -dihydroxy-20,19,18-trinoir-17-(4'-fluoro)-phenoxy-prost-5-en-13-ynoic acid;
5c-9-oxo-11α,15R-dihydroxy-20,19,18-trinor-17-(4'-fluoro)-phenyl-prost-5-en-13-ynoic acid;
5c-9oxo-11α,15R-dihydroxy-20,19,18-trinor-17-(3'-chloro)-phenyl-prost-5-en-13-ynoic acid;
5c-9-oxo-11α,15R-dihydroxy-20,19,18-trinor-17-(3'-trifluoromethyl)-phenyl-prost-5-en-13-ynoic acid;
5c-9-oxo-11α,15R-dihydroxy-20,19,18-trinor-17-(4'-methoxy)-phenyl-prost-5-en-13-ynoic acid;
5c-9-oxo-11α,15R-dihydroxy-20,19,18,17-tetranor-16-phenyl-prost-5-en-13-ynoic acid;
5c-9-oxo-11α,15Γ-dihydroxy-20,19-dinor-18phenyl-prost-5-en-13-ynoic acid;
5c-9-oxo-11α,15R-dihydroxy-20,19,18-trinor-17-phenyl-prost-5-en-13-ynoic acid;
5c-9-oxo-11α,15R-dihydroxy-20,19,18-trinor-16S-methyl-17-phenyl-prost-5-en-13-ynoic acid;
5c-9-oxo-11α,15R-dihydroxy-20,19,18-trinor-16R-methyl-17-phenyl-prost-5-en-13-ynoic acid;
5c-9-oxo-11α,15R-dihydroxy-20,19,18,17-tetranor-16S-methyl-16-phenoxy-prost-5-en-13-ynoic acid;

5c-9-oxo-11α,15R-dihydroxy-20,19,18,17-tetranor-16R-methyl-16-phenoxy-prost-5-en-13-ynoic acid;
5c-9-oxo-11α,15R-dihydroxy-20,19,18,17-tetranor-16-phenoxy-prost-5-en-13-ynoic acid;
5c-9-oxo-11α,15R-dihydroxy-20,19,18,17-tetranor-16-benzyloxy-prost-5-en-13-ynoic acid;
5c-9-oxo-11α,15R-dihydroxy-20,19,18,17-tetranor-16-(4'-methoxy)-phenoxy-prost-5-en-13-ynoic acid;
5c-9-oxo-11α,15R-dihydroxy-20,19,18,17-tetranor-16-(4'-fluoro)-phenoxy-prost-5-en-13-ynoic acid;
5c-9-oxo-11α,15R-dihydroxy-20,19,18,17-tetranor-16-(3'-chloro)-phenoxy-prost-5-en-13-ynoic acid;
5c-9-oxo-11α,15R-dihydroxy-20,19,18,17-tetranor-16-(3'-trifluoromethyl)-phenoxy-prost-5-en-13-ynoic acid;
5c-9-oxo-11α,15R-dihydroxy-20,19,18-trinor-17-(4'-fluoro)-phenoxy-prost-5-en-13-ynoic acid;
as well as the following 11-THP-ethers:
5c-9-oxo-11α-hydroxy-15S-methoxy-20,19,18-trinor-17-phenyl-prost-5-en-13-ynoic acid;
5c-9-oxo-11α-hydroxy-15S-ethoxy-20,19,18-trinor-17-phenyl-prost-5-en-13-ynoic acid;
5c-9-oxo-11α-hydroxy-15S-methoxy-20,19,18-trinor-16S-methyl-17-phenyl-prost-5-en-13-ynoic acid;
5c-9-oxo-11α-hydroxy-15S-methoxy-20,19,18-trinor-16R-methyl-17-phenyl-prost-5-en-13-ynoic acid;
5c-9-oxo-11α-hydroxy-15S-benzyloxy-20,19,18,17-tetranor-16-phenoxy-prost-5-en-13-ynoic acid;
5c-9oxo-11α-hydroxy-15R-methoxy-20,19,18-trinor-17-phenyl-prost-5-en-13-ynoic acid;
5c-9oxo-11α-hydroxy-15R-ethoxy-20,19,18-trinor-17-phenyl-prost-5-en-13-ynoic acid;
5c-9-oxo-11α-hydroxy-15R-methoxy-20,19,18-trinor-16S-methyl-17-phenyl-prost-5-en-13-ynoic acid;
5c-9-oxo-11α-hydroxy-15R-methoxy-20,19,18-trinor-16R-methyl-17-phenyl-prost-5-en-13ynoic acid;
5c-9oxo-11α-hydroxy-15R-benzyloxy-20,19,18,17-tetranor-16-phenoxy-prost-5-en-13-ynoic acid;
and the following compounds:
5c-9-oxo-11α,15S-dihydroxy-20,19,18,17-tetranor-16-(4'-fluoro)-phenoxy-prost-5-en-13-ynoic acid-11,15-bis-DIOX-ether;
5c-9-oxo-11α,15S-dihydroxy-20,19,18-trinor-17-phenyl-prost-5-en-13-ynoic acid-N,N-diethylamide-11,15-bis-THP-ether.
5c-9-oxo-11α,15R-dihydroxy-20,19,18,17-tetranor-16-(4'-fluoro)-phenoxy-prost-5-en-13-ynoic acid-11,15-bis-DIOX-ether;
5c-9-oxo-11α,15R-dihydroxy-20,19,18-trinor-17-phenyl-prost-5-en-13-ynoic-acid-N,N-diethylamide-11,15-bis-THP-ether.

EXAMPLE 33

A solution of 5c-9-oxo-11α-hydroxy-15S-methoxy-20,19,18-trinor-17-phenyl-prost-5-en-13-ynoic acid-11-THP-ether (0.2 g) in acetone (7 ml) was heated at 40° for 12 hours in the presence of 0.2N aqueous oxalic acid (5 ml). The acetone was evaporated in vacuum, and the resulting emulsion was extracted with ethyl ether. The organic extracts were washed until neutral with aqueous saturated $(NH_4)_2SO_4$, dried on $Na_2SO_4$ and evaporated to dryness. The residue was chromatographed on acid washed silica gel, using $CH_2Cl_2$-allyl acetate (80:20)as eluent, so obtaining 0.1 g of pure 5c-9-oxo-11α-hydroxy-15S-methoxy-20,19,18-trinor-17-phenyl-prost-5-en-13-ynoic acid$[α]_D = -23.7°$ $[α]_{365} = -64°$ (C=0.5% EtOH). Using this procedure in the deacetalization of the compounds of the Examples 30, 31 and 32, the following 9-oxo-11α-hydroxy-prostanoic acids were obtained:
5c-9-oxo-11α,15S-dihydroxy-20,19,18-trinor-17-(4'-fluoro)-phenyl-prost-5-en-13-ynoic acid;
5c-9-oxo-11α,15S-dihydroxy-20,19,18-trinor-17-(3'-chloro)-phenyl-prost-5-en-13-ynoic acid;
5c-9-oxo-11α,15S-dihydroxy-20,19,18-trinor-17-(3'-trifluoro-methyl)-phenyl-prost-5-en-13-ynoic acid;
5c-9-oxo-11α,15S-dihydroxy-20,19,18-trinor-17-(4'-methoxy)-phenyl-prost-5-en-13-ynoic acid;
5c-9-oxo-11α,15S-dihydroxy-20,19,18,17-tetranor-16-phenyl-prost-5-en-13-ynoic acid;
5c-9-oxo-11α,15S-dihydroxy-20,19-dinor-18-phenyl-prost-5-en-13-ynoic acid;
5c-9-oxo-11α,15S-dihydroxy-20,19,18-trinor-17-phenyl-prost-5-en-13-ynoic acid;
5c-9-oxo-11α,15S-dihydroxy-20,19,18-trinor-16S-methyl-17-phenyl-prost-5-en-13-ynoic acid;
5c-9-oxo-11α,15S-dihydroxy-20,19,18-trinor-16R-methyl-17-phenyl-prost-5-en-13-ynoic acid;
5c-9-oxo-11α,15S-dihydroxy-20,19,18,17-tetranor-16S-methyl-16-phenoxy-prost-5-en-13-ynoic acid;
5c-9-oxo-11α,15S-dihydroxy-20,19,18,17-tetranor-16R-methyl-16-phenoxy-prost-5-en-13-ynoic acid;
5c-9-oxo-11α,15S-dihydroxy-20,19,18,17-tetranor-16-phenoxy-prost-5-en-13-ynoic acid;
5c-9-oxo-11α,15S-dihydroxy-20,19,18,17-tetranor-16-benzyloxy-prost-5-en-13-ynoic acid;
5c-9-oxo-11α,15S-dihydroxy-20,19,18,17-tetranor-16-(4'-methoxy)-phenoxy-prost-5-en-13-ynoic acid;
5c-9-oxo-11α,15S-dihydroxy-20,19,18,17-tetranor-16-(4'-fluoro)-phenoxy-prost-5-en-13-ynoic acid;
5c-9-oxo-11α,15S-dihydroxy-20,19,18,17-tetranor-16-(3'-chloro)-phenoxy-prost-5-en-13-ynoic acid;
5c-9-oxo-11α,15S-dihydroxy-20,19,18,17-tetranor-16-(3'-trifluoromethyl)-phenoxy-prost-5-en-13-ynoic acid;
5c-9-oxo-11α,15S-dihydroxy-20,19,18-trinor-17-(4'-fluoro)-phenoxy-prost-5-en-13-ynoic acid;
5c-9-oxo-11α,15R-dihydroxy-20,19,18-trinor-17-(4'-fluoro)-phenyl-prost-5-en-13-ynoic acid;
5c-9-oxo-11α,15R-dihydroxy-20,19,18-trinor-17-(3'-chloro)-phenyl-prost-5-en-13-ynoic acid;
5c-9-oxo-11α,15R-dihydroxy-20,19,18-trinor-17-(3'-trifluoromethyl)-phenyl-prost-5-en-13-ynoic acid;
5c-9-oxo-11α,15R-dihydroxy-20,19,18-trinor-17-(4'-methoxy)-phenyl-prost-5-en-13-ynoic acid;
5c-9-oxo-11α,15R-dihydroxy-20,19,18,17-tetranor-16-phenyl-prost-5-en-13-ynoic acid;
5c-9-oxo-11α,15R-dihydroxy-20,19-dinor-18-phenyl-prost-5-en-13-ynoic acid;
5c-9-oxo-11α,15R-dihydroxy-20,19,18-trinor-17-phenyl-prost-5-en-13-ynoic acid;
5c-9-oxo-11α,15R-dihydroxy-20,19,18-trinor-16S-methyl-17-phenyl-prost-5-en-13-ynoic acid;
5c-9-oxo-11α,15R-dihydroxy-20,19,18-trinor-16R-methyl-17-phenyl-prost-5-en-13-ynoic acid;
5c-9-oxo-11α,15R-dihydroxy-20,19,18,17-tetranor-16S-methyl-16-phenoxy-prost-5-en-13-ynoic acid;
5c-9-oxo-11α,15R-dihydroxy-20,19,18,17-tetranor-16R-methyl-16-phenoxy-prost-5-en-13-ynoic acid;
5c-9-oxo-11α,15R-dihydroxy-20,19,18,17-tetranor-16-phenoxy-prost-5-en-13-ynoic acid;
5c-9-oxo-11α,15R-dihydroxy-20,19,18,17-tetranor-16-benzyloxy-prost-5-en-13-ynoic acid;
5c-9-oxo-11α,15R-dihydroxy-20,19,18,17-tetranor-16-(4'-methoxy)-phenoxy-prost-5-en-13-ynoic acid;

5c-9-oxo-11α,15R-dihydroxy-20,19,18,17-tetranor-16-(4'-fluoro)-phenoxy-prost-5-en-13-ynoic acid;

5c-9-oxo-11α,15R-dihydroxy-20,19,18,17-tetranor-16-(3'-chloro)-phenoxy-prost-5-en-13-ynoic acid;

5c-9-oxo-11α,15R-dihydroxy-20,19,18,17-tetranor-16-(3'-trifluoromethyl)-phenoxy-prost-5-en-13-ynoic acid;

5c-9-oxo-11α,15R-dihydroxy-20,19,18-trinor-17(4'-fluoro)-phenoxy-prost-5-en-13-ynoic acid;

5c-9-oxo-11α-hydroxy-15S-methoxy-20,19,18-trinor-17-phenyl-prost-5-en-13-ynoic acid;

5c-9-oxo-11α-hydroxy-15S-ethoxy-20,19,18-trinor-17-phenyl-prost-5-en-13-ynoic acid;

5c-9-oxo-11α-hydroxy-15S-methoxy-20,19,18-trinor-16S-methyl-17-phenyl-prost-5-en-13-ynoic acid;

5c-9-oxo-11α-hydroxy-15S-methoxy-20,19,18-trinor-16R-methyl-17-phenyl-prost-5-en-13-ynoic acid;

5c-9-oxo-11α-hydroxy-15S-benzyloxy-20,19,18,17-tetranor-16-phenoxy-prost-5-en-13-ynoic acid;

5c-9-oxo-11α-hydroxy-15R-methoxy-20,19,18-trinor-17-phenyl-prost-5-en-13-ynoic acid;

5c-9-oxo-11α-hydroxy-15R-ethoxy-20,19,18-trinor-17-phenyl-prost-5-en-13-ynoic acid;

5c-9-oxo-11α-hydroxy-15R-methoxy-20,19,18-trinor-16S-methyl-17-phenyl-prost-5-en-13-ynoic acid;

5c-9-oxo-11α-hydroxy-15R-methoxy-20,19,18-trinor-16R-methyl-17-phenyl-prost-5-en-13-ynoic acid;

5c-9-oxo-11α-hydroxy-15R-benzyloxy-20,19,18,17-tetranor-16-phenoxy-prost-5-en-13-ynoic acid;

5c-9-oxo-11α,15S-dihydroxy-20,19,18-trinor-17-phenyl-prost-5-en-13-ynoic acid-N,N-diethylamide;

5c-9-oxo-11α,15R-dihydroxy-20,19,18-trinor-17-phenyl-prost-5-en-13-ynoic acid.

EXAMPLE 34

A solution of 5c-9-oxo-11α,15S-dihydroxy-20,19,18-trinor-17-phenyl-prost-5-en-13-ynoic acid-11,15-bis-THP-ether (0.55 g) in acetone (10 ml) was refluxed with 6 ml of a 0.15 N aqueous oxalic acid for 6 hours.

The excess acetone was removed in vacuo and the solution was extracted with ether. The organic extract was concentrated and absorbed on acid-washed silica gel. Elution with benzene ethyl ether afforded 0.18 g of 5c-9-oxo-15S-hydroxy-20,19,18-trinor-17-phenyl-prost-5,10-dien-13-ynoic acid.

The methyl ester of this compound was obtained when deacetalization was accomplished in methanol (15 ml) in the presence of p-toluenesulfonic acid (30 mg).

Analogously, starting from the corresponding 9-oxo-11α-acetalic ether, the following compounds:

5c-9-oxo-15S-methoxy-20,19,18-trinor-17-phenyl-prosta-5,10-dien-13-ynoic acid;

5c-9-oxo-15S-hydroxy-20,19,18,17-tetranor-16-phenoxy-prosta-5,10-dien-13-ynoic acid were prepared.

EXAMPLE 35

A solution of 5c-9α,11α-dihydroxy-15S-methoxy-20,19,18-trinor-17-phenyl-prost-5-en-13-ynoic acid-11,15-bis-THP-ether in acetone (10 ml) and 0.2 N aqueous oxalic acid (10 ml) was heated at 40° C. for 12 hours and then the acetone was removed in vacuum. The aqueous phase was extracted with ethyl acetate, and after washing until neutral, the organic layer was dried and evaporated to dryness. The residue was chromatographed on acid-washed silica gel (30 g) and elution with methylene chloride-ethyl acetate (80:20) afforded 5c-9α,11α-dihydroxy-15S-methoxy-20,19,18-trinor-17-phenyl-prost-5-en-13-ynoic acid $[\alpha]_D = +19.5°$ (EtOH).

EXAMPLE 36

A solution of 5c-9α,11α,15S-trihydroxy-20,19,18-trinor-17-phenyl-prost-5-en-13-ynoic acid-11,15-bis-THP-ether (0.8 g) was dissolved in dry methanol (10 ml) and treated with p-toluenesulfonic acid (30 mg).

After 4 hours, the methanol was evaporated in vacuum and the oil was partitioned between water and ethyl acetate. The organic layer was washed with 2.5 ml of 5% NaHCO$_3$, water and evaporated to dryness.

The residue was absorbed on silica gel and eluted with benzene-ether (50:50) affording 0.48 g of methyl 5c-9α,11α,15S-trihydroxy-20,19,18-trinor-17-phenyl-prost-5-en-13-ynoate, $[\alpha]_D = +44.6°$ $[\alpha]_{365} = +148°$ (EtOH).

A solution of this compound (0.2 g) was treated in aqueous methanol (20:80) with lithium hydroxide (0.04 g) for 4 hours at room temperature.

The methanol was removed in vacuum. The aqueous alkaline phase was extracted with ethyl ether to remove impurities, then acidified to pH 5.1 with aqueous NaH$_2$PO$_4$ solution and extracted with ethyl ether.

These extracts were dried on Na$_2$SO$_4$, evaporated to dryness affording pure 5c-9α,11α,15S-trihydroxy-20,19,18-trinor-17-phenyl-prost-5-en-13-ynoic acid, $[\alpha]_D = +46.7°$ $[\alpha]_{365} = +155°$ (EtOH C=1%).

EXAMPLE 37

Using in the procedure of the Example 36 absolute ethanol as solvent to deacetalize, the ethyl-5c-9α,11α,15S-trihydroxy-20,19,18-trinor-17-phenyl-prost-5-en-13-ynoate, $[\alpha]_D = +42°$ (EtOH) was prepared.

EXAMPLE 38

Methyl 5c-9α,11α,15S-trihydroxy-20,19,18,17-tetranor-16-(3'-trifluoromethyl)-phenoxy-prost-5-en-13-ynoate, $[\alpha]_D = +15.7°$ (EtOH) was prepared by deacetalization of its 11,15-bis-THP-ether (according to Example 35), followed by purification on silica gel [4.5 g, using CH$_2$Cl$_2$:ethylacetate (65:35) as eluent].

EXAMPLE 39

Using in the procedure of Example 35 and 38, the free acid, the 5c-9α,11α, 15S-trihydroxy-20,19,18,17-tetranor-16-(4'-fluoro)-phenoxy-prost-5-en-13-ynoic acid, $[\alpha]_D = +15.6, [\alpha]_{365} = +53.4°$ (EtOH C=1%) was prepared.

EXAMPLE 40

Using in the deacetalization of a 9-hydroxy-11- or 11,15-acetalic prostynoic derivative prepared in the Examples 24-28, a polycarboxylic acid according to Examples 35, 38 and 39, or a solution of p-toluenesulfonic acid in a dry alcohol according to Examples 36 and 37 and after purification on silica gel column, the following compounds were prepared either as free acids or as methyl or ethyl esters:

5c-9α,11α,15S-trihydroxy-20,19,18-trinor-17-(4'-fluoro)-phenyl -prost-5-en-13-ynoic acid; 5c-9α,11α, 15S-trihydroxy-20,19,18-trinor-17-(3'-chloro)-phenyl-prost-5-en-13-ynoic acid;

5c-9α,11α,15S-trihydroxy-20,19,18-trinor-17-(3'-trifluoromethyl)-phenyl-prost-5-en-13-ynoic acid;

5c-9α,11α,15S-trihydroxy-20,19,18-trinor-17-(4'-methoxy)-phenyl-prost-5-en-13-ynoic acid;

5c-9α,11α,15S-trihydroxy-20,19,18,17-tetranor-16-phenyl-prost-5-en-13-ynoic acid;

5c-9α,11α,15S-trihydroxy-20,19-ω-nor-18-phenyl-prost-5-en-13-ynoic acid;

5c-9α,11α,15S-trihydroxy-20,19,18-trinor-17-phenyl-prost-5-en-13-ynoic acid;

5c-9α,11α,15S-trihydroxy-20,19,18-trinor-16S-methyl-17-phenyl-prost-5-en-13-ynoic acid;

5c-9α,11α-15S-trihydroxy-20,19,18-trinor-16R-methyl-17-phenyl-prost-5-en-13-ynoic acid;

5c-9α,11α,15S-trihydroxy-20,19,18,17-tetranor-16S-methyl-16-phenoxy-prost-5-en-13-ynoic acid;

5c-9α,11α,15S-trihydroxy-20,19,18,17-tetranor-16R-methyl-16-phenoxy-prost-5-en-13ynoic acid;

5c-9α, 11α,15S-trihydroxy-20,19,18,17-tetranor-16-benzyloxy-prost-5-en-13-ynoic acid;

5c-9α,11α,15S-trihydroxy-20,19,18,17-tetranor-16-phenoxy-prost-5-en-13-ynoic acid;

5c-9α,11α,15S-trihydroxy-20,19,18,17-tetranor-16-(4'-methoxy)-phenoxy-prost-5-en-13-ynoic acid;

5c-9α,11α,15S-trihydroxy-20,19,18,17-tetranor-16-(4'-fluoro)-phenoxy-prost-5-en-13-ynoic acid;

5c-9α,11α,15S-trihydroxy-20,19,18,17-tetranor-16-(3'-chloro)-phenoxy-prost-5-en-13-ynoic acid;

5c-9α11α,15S-trihydroxy-20,19,18,17-tetranor-16-(3'-trifluoromethyl)-phenoxy-prost-5-en-13-ynoic acid;

5c-9α,11α,15S-trihydroxy-20,19,18-trinor-17-(4'-fluoro)-phenoxy-prost-5-en-13-ynoic acid;

5c-9α,11α,15R-trihydroxy-20,19,18-trinor-17-(4'-fluoro)-phenyl-prost-5-en-13-ynoic acid;

5c-9α,11α,15R-trihydroxy-20,19,18-trinor-17-(3'-chloro)-phenyl-prost-5-en-13-ynoic acid;

5c-9α,11α,15R-trihydroxy-20,19,18-trinor-17-(3'-trifluoromethyl)-phenyl-prost-5-en-13-ynoic acid;

5c-9α,11α,15R-trihydroxy-20,19,18-trinor-17-(4'-methoxy)-phenyl-prost-5-en-13-ynoic acid;

5c-9α,11α,15R-trihydroxy-20,19,18,17-tetranor-16-phenyl-prost-5-en-13-ynoic acid;

5c-9α,11α,15R-trihydroxy-20,19-ω-nor-18-phenyl-prost-5-en-13-ynoic acid;

5c-9α,11α,15R-trihydroxy-20,19,18-trinor-17-phenyl-prost-5-en-13-ynoic acid;

5c-9α,11α,15R-trihydroxy-20,19,18-trinor-16S-methyl-17-phenyl-prost-5-en-13-ynoic acid;

5c-9α,11α-15R-trihydroxy-20,19,18-trinor-16R-methyl-17-phenyl-prost-5-en-13-ynoic acid;

5c-9α,11α,15R-trihydroxy-20,19,18,17-tetranor-16S-methyl-16-phenoxy-prost-5-en-13-ynoic acid;

5c-9α,11α,15R-trihydroxy-20,19,18,17-tetranor-16R-methyl-16-phenoxy-prost-5-en-13-ynoic acid;

5c-9α,11α,15R-trihydroxy-20,19,18,17-tetranor-16-benzyloxy-prost-5-en-13-ynoic acid;

5c-9α,11α,15R-trihydroxy-20,19,18,17-tetranor-16-phenoxy-prost-5-en-13-ynoic acid;

5c-9α,11α,15R-trihydroxy-20,19,18,17-tetranor-16-(4'-methoxy)-phenoxy-prost-5-en-13-ynoic acid;

5c-9α,11α,15R-trihydroxy-20,19,18,17-tetranor-16-(4'-fluoro)-phenoxy-prost-5-en-13-ynoic acid;

5c-9α,15R-trihydroxy-20,19,18,17-tetranor-16-(3'-chloro)-phenoxy-prost-5-en-13-ynoic acid;

5c-9α11α,15R-trihydroxy-20,19,18,17-tetranor-16-(3'-trifluoromethylphenoxy-prost-5-en-13-ynoic acid;

5c-9α,11α,15R-trihydroxy-20,19,18-trinor-17-(4'-fluoro)phenoxy-prost-5-en-13-ynoic acid;

5c-9α,11α-dihydroxy-15S-methoxy-20,19,18-trinor-17-phenyl-prost-5-en-13-ynoic acid;

5c-9α,11α-dihydroxy-15S-ethoxy-20,19,18-trinor-17-phenyl-prost-5-en-13-ynoic acid;

5c-9α,11α-dihydroxy-15S-methoxy-20,19,18-trinor-16S-methyl-17-phenol-prost-5-en-13-ynoic acid;

5c-9α,11α-dihydroxy-15S-methoxy-10,19,18-trinor-16R-methyl-17-phenyl-prost-5-en-13-ynoic acid;

5c-9α,11α-dihydroxy-15S-benzyloxy-20,19,18,17-tetranor-16-phenoxy-prost-5-en-13-ynoic acid;

5c-9α,11α-dihydroxy-15R-methoxy-20,19,18-trinor-17-phenyl-prost-5-en-13-ynoic acid;

5c-9α,11α-dihydroxy-15R-ethoxy-29,19,18-trinor-17-phenyl-prost-5-en-13-ynoic acid;

5c-9α,11α-dihydroxy-15R-methoxy-20,19,18-trinor-16S-methyl-17-phenyl-prost-5-en-13-ynoic acid;

5c-9α,11α-dihydroxy-15R-methoxy-20,19,18-trinor-16R-methyl-17-phenyl-5-en-13-ynoic acid;

5c-9α,11α-dihydroxy-15R-benzyloxy-20,19,18,17-tetranor-16-phenoxy-prost-5-en-13-ynoic acid.

EXAMPLE 41

Using in the deacetalization of a 9-hydroxy-11- or 11,15-acetalic prost-ynoic derivative prepared in the Example 29, a poly-carboxylic acid according to Examples 35, 38 and 39, or a solution of p-toluenesulfonic acid in a dry alcohol according to Examples 36 and 37 and after purification on silica gel column, the following compounds were prepared:

5c-9β,11α,15S-trihydroxy-20,19,18-trinor-17-phenyl-prost-5-en-13-ynoic acid-9-benzoate-methyl ester, 5c-9β,11α,15S-trihydroxy-20,19,18,17-tetranor-16-(4'-fluoro)-phenoxy-prost-5-en-13-ynoic acid-9-benzoate-methyl ester, 5c-9β,11α-dihydroxy-15S-methoxy-20,19,18-trinor-17-phenyl-prost-5-en-13-ynoic acid-9-benzoate-methyl ester, 5c-9β,11α,15S-trihydroxy-20,19,18-trinor-17-phenyl-prost-5-en-13-ynoic acid-methyl ester, 5c-9β,11α,15S-trihydroxy-20,19,18,17-tetranor-16-(4'-fluoro)-phenoxy-prost-5-en-ynoic acid-methyl ester, 5c-9β,11α-dihydroxy-15S-methoxy-20,19,18-trinor-17-phenyl-prost-5-en-13-ynoic acid methyl ester, which by saponification with sodium hydroxide in aqueous ethanol under reflux were converted into the corresponding free hydroxy acids.

EXAMPLE 42

5c-1,9α,11α,15S-tetrahydroxy-20,19,18-trinor-17-phenyl-prost-5-en-13-yne, $[\alpha]_D = +49.8°$ $[\alpha]_{365} = +128.5°$ (0.32 g) was obtained starting from a solution of the corresponding 1-carboxy-methyl ester (0.45 g) in dry ethyl ether, which was added dropwise to a stirred solution of 0.06 g of LiAlH$_4$ in ethyl ether, cooling to $-2° + +3°$. After 3 hours, the excess reagent was destroyed by slow addition of aqueous saturated NH$_4$Cl solution. The organic layer was separated, evaporated to dryness and the residue was absorbed on silica gel (5 g). Elution by cyclohexane-ethylacetate afforded the compound. Same compound was obtained starting from a solution of the 5β-(2'-bromo-3'-S-hydroxy-5'-phenyl-pent-1'-trans-1'enyl)-2α,4α-dihydroxy-cyclopentane-1α-ethanal-γ-lactol-3',4-bis-THP-ether (0.8 g) in dry DMSO (5 ml) which was treated with the ylide prepared in dry DMSO by adding a solution of potassium tert-butoxide (0.7 g) in DMSO (7 ml) to a stirred solution of triphenyl [5-(2'-tetrahydropyranyloxy)-pentyl]-phosphonium bromide in dry DMSO, cooled at 12°–14° C.

The mixture was maintained for 8 hours at room temperature, then was diluted with water and extracted with ethyl ether:pentane (1:1). The organic extracts were washed until neutral, dried on $Na_2SO_4$, evaporated and the residue was chromatographed on silica gel to afford 5c-1,9α,11α,15S-tetrahydroxy-20,19,18-trinor-17-phenyl-prost-5-en-13-yne-1,11,15-tris-THP-ether (0.71 g).

A solution of this compound (0.34 g) was then treated in dry methanol (10 ml) with p-toluenesulfonic acid (10 mg). After 3 hours it was evaporated to dryness affording the free tetrahydroxy compound, $[α]_D = +40.8°$.

EXAMPLE 43

A solution of 5c-1,9α,11α15S-tetrahydroxy-20,19,18-trinor-17-phenyl-prost-5-en-13-yne-1,11,15-tris-THP-ether (0.42 g) in acetone (12 ml), cooled to $-10 + -13°$, was reacted with 0.8 ml of Jones reagent and added dropwise to the stirred mixture. After 20 minutes, the reaction was stopped by addition of excess benzene (80 ml) and the organic phase was washed with 35% aqueous $(NH_4)_2SO_4$ solution until neutral, and evaporated to dryness. The residual 9-oxo compound was dissolved in acetone (20 ml) and the solution was heated at 42° C. after addition of 0.15N oxalic acid (15 ml) for 14 hours. The excess acetone was evaporated in vacuum. The aqueous phase was extracted with ethyl acetate and after chromatographic separation on silica gel (using as eluent cyclohexane/ethylacetate 65:35), 5c-9-oxo-1,11α,15S-trihydroxy-20,19,18-trinor-17-phenyl-prost-5-en-13-yne (0.16 g) was obtained.

EXAMPLE 44

Using the procedure of the Examples 42 and 43 the following compounds were prepared:
5c-9-oxo-1,11α,15S-trihydroxy-16S-methyl-20,19,18-trinor-17-phenyl-prost-5-en-13-yne;
5c-9-oxo-1,11α-dihydroxy-15S-methoxy-20,19,18-trinor-17-phenyl-prost-5-en-13-yne;
5c-1,9α,11α-trihydroxy-15S-methoxy-20,19,18-trinor-17-phenyl-prost-5-en-13-yne;
5c-1,9α,11α,15S-tetrahydroxy-16S-methyl-20,19,18-trinor-17-phenyl-prost-5-en-13-yne;
5c-1,9α,11α,15S-tetrahydro-29,19,18,17-tetranor-16-(4'-fluoro)-phenoxy-prost-5-en-13-yne;
5c-1,9α,11α,15S-tetrahydroxy-20,19,18,17-tetranor-16-phenoxy-prost-5-en-13-yne;
5c-1,9α,11α,15S-tetrahydroxy-20,19,18,17-tetranor-16-(3'-trifluoromethyl)-phenoxy-prost-5-en-13-yne;
5c-1,9α,11α,15S-tetrahydroxy-20,19,18,17-tetranor-16-(3'-m-chloro)-phenoxy-prost-5-en-13-yne.

We claim:
1. An optically active or racemic $PGF_α$ compound of the formula

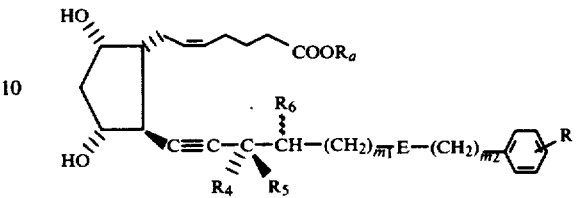

wherein:
$R_a$ is hydrogen, $C_1$–$C_{12}$ alkyl or a cation of a pharmaceutically of veterinarily acceptable base;
one of $R_4$ and $R_5$ is hydrogen and the other is hydroxyl or $C_1$–$C_6$ alkoxy;
$R_6$ is hydrogen or $C_1$–$C_4$ alkyl;
each of $m_1$ and $m_2$ is independently zero, 1, 2 or 3;
E is oxygen or sulphur
R is hydrogen, halogen, $C_1$–$C_6$ alkyl, $C_1$–$C_6$ alkoxy or $C_1$–$C_6$ trihaloalkyl.

2. A compound selected from the group consisting of:
5c-9α,11α,15S-trihydroxy-20,19,18,17-tetranor-16-phenoxy-prost-5-en-13-ynoic acid;
5c-9α,11α,15S-trihydroxy-20,19,18,17-tetranor-16-(4'-fluoro)-phenoxy-prost-5-en-13-ynoic acid;
5c-9α,11α,15S-trihydroxy-20,19,18,17-tetranor -16-(3'-chloro)-phenoxy-prost-5-en-13-ynoic acid;
5c-9α,11α,15S-trihydroxy-20,19,18,17-tetranor-16-(3'-trifluoromethyl)-phenoxy-prost-5-en-13-ynoic acid;
5c-9α,11α,15S-trihydroxy-20,19,18,17-tetranor-16(2'-fluoro)-phenoxy-prost-5-en-13-ynoic acid;
5c-9α,11α,15S-trihydroxy-20,19,18,17-tetranor-16-(2'-methoxy)-phenoxy-prost-5-en-13-ynoic acid;
5c-9α,11α,15S-trihydroxy-20,19,18,17-tetranor-16S-methyl-16-phenoxy-prost-5-en-13-ynoic acid;
5c-9α,11α,15S-trihydroxy-20,19,18,17-tetranor-16R-methyl-16-phenoxy-prost-5-en-13-ynoic acid;
and the salts and the lower alkyl esters thereof.

3. A pharmaceutical or veterinary composition comprising a suitable carrier and/or diluent, and, as an active principle, a compound of claim 1.

* * * * *